(12) United States Patent
Kwon et al.

(10) Patent No.: US 12,122,845 B2
(45) Date of Patent: Oct. 22, 2024

(54) ANTI-HER2/ANTI-4-1BB BISPECIFIC ANTIBODIES AND USES THEREOF

(71) Applicant: EUTILEX CO., LTD., Seoul (KR)

(72) Inventors: Byoung S. Kwon, Seoul (KR); Hanna Lee, Seoul (KR); Yeonji Oh, Seoul (KR); Jin Sung Park, Seoul (KR)

(73) Assignee: Eutilex Co., Ltd., Seoul (KR)

( * ) Notice: Subject to any disclaimer, the term of this patent is extended or adjusted under 35 U.S.C. 154(b) by 0 days.

(21) Appl. No.: 17/397,559

(22) Filed: Aug. 9, 2021

(65) Prior Publication Data

US 2022/0041750 A1     Feb. 10, 2022

Related U.S. Application Data

(60) Provisional application No. 63/062,697, filed on Aug. 7, 2020.

(51) Int. Cl.
| | | |
|---|---|---|
| *C07K 16/00* | (2006.01) | |
| *A61P 35/00* | (2006.01) | |
| *C07K 16/28* | (2006.01) | |
| *C07K 16/32* | (2006.01) | |
| *A61K 39/00* | (2006.01) | |

(52) U.S. Cl.
CPC ............... *C07K 16/32* (2013.01); *A61P 35/00* (2018.01); *C07K 16/2878* (2013.01); *A61K 2039/505* (2013.01); *C07K 2317/21* (2013.01); *C07K 2317/24* (2013.01); *C07K 2317/31* (2013.01); *C07K 2317/51* (2013.01); *C07K 2317/515* (2013.01); *C07K 2317/522* (2013.01); *C07K 2317/56* (2013.01); *C07K 2317/622* (2013.01); *C07K 2317/92* (2013.01)

(58) Field of Classification Search
CPC ............... C07K 16/32; C07K 16/2878; C07K 2317/21; C07K 2317/24; C07K 2317/31; C07K 2317/51; C07K 2317/515; C07K 2317/56; C07K 2317/622; A61P 35/00; A61K 2039/505

See application file for complete search history.

(56) References Cited

U.S. PATENT DOCUMENTS

| 10,174,122 B2 | 1/2019 | Kwon et al. | |
|---|---|---|---|
| 2018/0258177 A1* | 9/2018 | Kwon | C07K 16/2878 |
| 2021/0024650 A1* | 1/2021 | Chung | A61P 35/00 |

FOREIGN PATENT DOCUMENTS

| WO | WO2003031464 | * | 4/2003 |
|---|---|---|---|
| WO | WO 2016/177802 A1 | | 11/2016 |
| WO | WO 2017/182672 A1 | | 10/2017 |

OTHER PUBLICATIONS

Hinner et al (Clinical Cancer Research online published May 28, 2019 (Year: 2019).*
International Search Report and Written Opinion issued Dec. 17, 2021 in PCT/IB2021/000543, 13 pages.
Marlon J. Hinner, et al., "Tumor-Localized Costimulatory T-Cell Engagement by the 4-1BB/HER2 Bispecific Antibody-Anticalin Fusion PRS-343," Clinical Cancer Research, vol. 25, No. 19, Oct. 1, 2019, 13 pages.
Marlon J. Hinner, et al., "Costimulatory T cell engagement via a novel bispecific anti-CD137/anti-HER2 protein," Journal for Immuno Therapy of Cancer, vol. 3, 2015, p. 187.

* cited by examiner

*Primary Examiner* — Lei Yao

(74) *Attorney, Agent, or Firm* — Haynes and Boone, LLP

(57) ABSTRACT

A bispecific epitope binding protein having a multimer of four single-chain chimeric polypeptides of two single-chain chimeric heavy chains and two single-chain chimeric light chains. The bispecific epitope binding protein has a first antigen binding domain that binds specifically to HER2 and a second antigen binding domain that binds specifically to 4-1BB.

25 Claims, 19 Drawing Sheets

Specification includes a Sequence Listing.

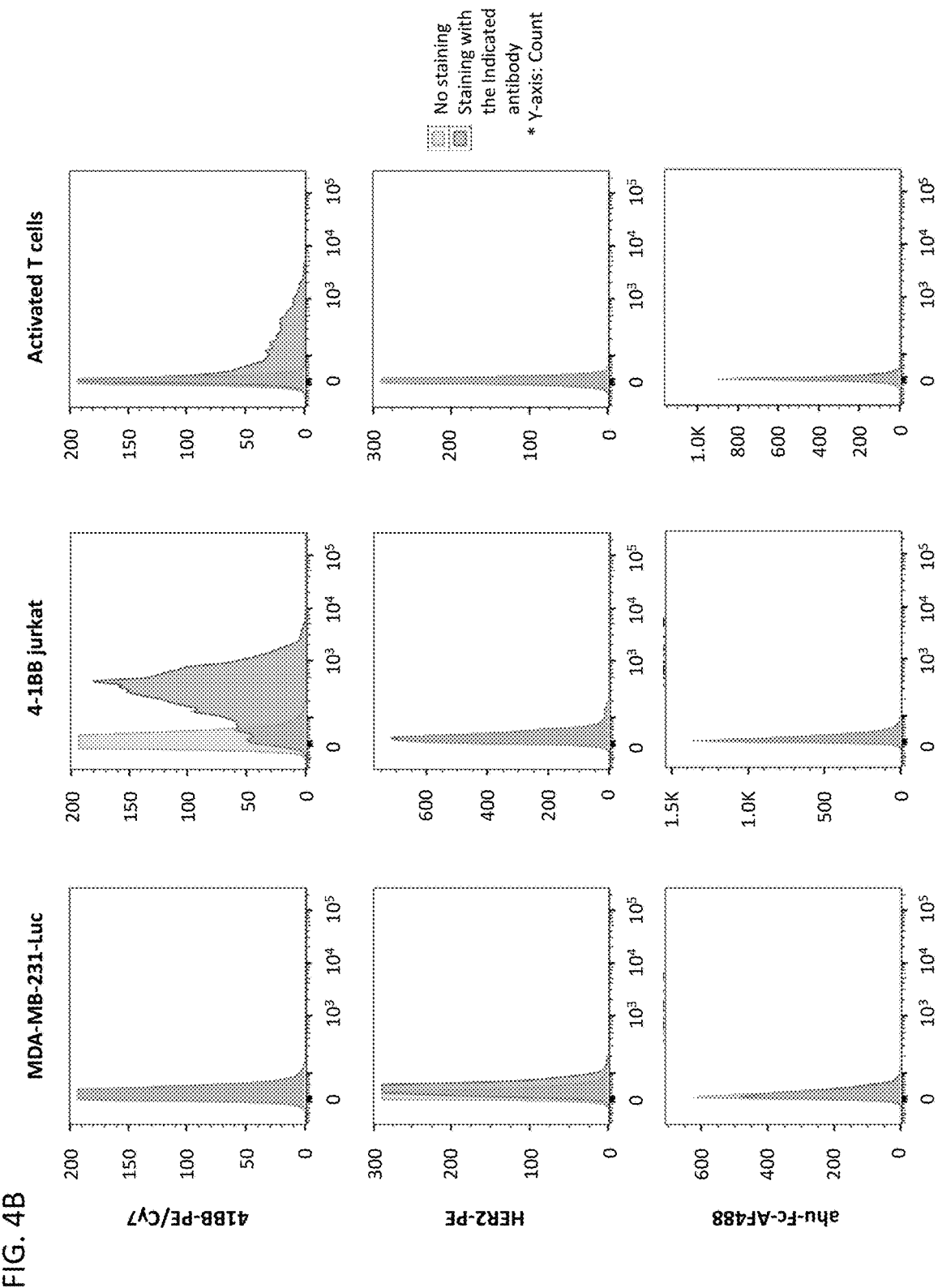

| | SKBR3 | SKOV3 | MCF7 | MDA-MB-231 | 41BB Jurkat | Activated T cell |
|---|---|---|---|---|---|---|
| HER2 | +++++ | ++++ | ++ | + | - | - |
| 41BB | - | - | - | - | +++ | ++ |

FIG. 4C

SEQUENCE LISTING

<160> NUMBER OF SEQ ID NOS: 13

<210> SEQ ID NO 1
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 2
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 3
<211> LENGTH: 118
<212> TYPE: PRT
<213> ORGANISM: Artificial Sequence
<220> FEATURE:
<223> OTHER INFORMATION: Synthetic Peptide -continued

<400> SEQUENCE: 3

Gln Val Gln Leu Val Gln Ser Gly Ala Glu Val Lys Lys Pro Gly Ala
1               5                   10                  15

Ser Val Lys Leu Ser Cys Lys Ala Ser Gly Tyr Thr Phe Ser Ser Tyr
            20                  25                  30

Trp Met His Trp Val Arg Gln Ala Pro Gly Gln Gly Leu Glu Trp Ile
        35                  40                  45

Gly Glu Ile Asn Pro Asn Gly His Thr Asn Tyr Asn Glu Lys Phe Lys
    50                  55                  60

Ser Arg Val Thr Met Thr Arg Asp Thr Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Ser Phe Lys Thr Ala Arg Ala Phe Ala Tyr Trp Gly Gln Gly Thr
            100                 105                 110

Leu Val Thr Val Ser Ser
            115

<210> SEQ ID NO 4
<211> LENGTH: 107
<212> TYPE: PRT
<213> ORGANISM: Artificial Sequence
<220> FEATURE:
<223> OTHER INFORMATION: Synthetic Peptide

<400> SEQUENCE: 4

Asp Ile Val Met Thr Gln Ser Pro Ala Phe Leu Ser Val Thr Pro Gly
1               5                   10                  15

Glu Lys Val Thr Ile Thr Cys Arg Ala Ser Gln Thr Ile Ser Asp Tyr
            20                  25                  30

Leu His Trp Tyr Gln Gln Lys Pro Asp Gln Ala Pro Lys Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Phe Thr Ile Ser Ser Leu Glu Ala
65                  70                  75                  80

Glu Asp Ala Ala Thr Tyr Tyr Cys Gln Asp Gly His Ser Trp Pro Pro
                85                  90                  95

Thr Phe Gly Gln Gly Thr Lys Leu Glu Ile Lys
            100                 105

<210> SEQ ID NO 5
<211> LENGTH: 717
<212> TYPE: PRT
<213> ORGANISM: Artificial Sequence
<220> FEATURE:
<223> OTHER INFORMATION: Synthetic Peptide

<400> SEQUENCE: 5

Met Glu Trp Ser Trp Val Phe Leu Val Thr Leu Leu Asn Gly Ile Gln
1               5                   10                  15

Cys Glu Val Gln Leu Val Glu Ser Gly Gly Gly Leu Val Gln Pro Gly
            20                  25                  30

Gly Ser Leu Arg Leu Ser Cys Ala Ala Ser Gly Phe Asn Ile Lys Asp
        35                  40                  45

Thr Tyr Ile His Trp Val Arg Gln Ala Pro Gly Lys Gly Leu Glu Trp
    50                  55                  60

```
Val Ala Arg Ile Tyr Pro Thr Asn Gly Tyr Thr Arg Tyr Ala Asp Ser
 65                  70                  75                  80

Val Lys Gly Arg Phe Thr Ile Ser Ala Asp Thr Ser Lys Asn Thr Ala
                 85                  90                  95

Tyr Leu Gln Met Asn Ser Leu Arg Ala Glu Asp Thr Ala Val Tyr Tyr
            100                 105                 110

Cys Ser Arg Trp Gly Gly Asp Gly Phe Tyr Ala Met Asp Tyr Trp Gly
        115                 120                 125

Gln Gly Thr Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Pro Val Ala Gly
                245                 250                 255

Pro Ser Val Phe Leu Phe Pro Pro Lys Pro Lys Asp Thr Leu Met Ile
            260                 265                 270

Ser Arg Thr Pro Glu Val Thr Cys Val Val Val Asp Val Ser His Glu
        275                 280                 285

Asp Pro Glu Val Gln Phe Asn Trp Tyr Val Asp Gly Val Glu Val His
    290                 295                 300

Asn Ala Lys Thr Lys Pro Arg Glu Glu Gln Phe Asn Ser Thr Phe Arg
305                 310                 315                 320

Val Val Ser Val Leu Thr Val Val His Gln Asp Trp Leu Asn Gly Lys
                325                 330                 335

Glu Tyr Lys Cys Lys Val Ser Asn Lys Gly Leu Pro Ala Pro Ile Glu
            340                 345                 350

Lys Thr Ile Ser Lys Thr Lys Gly Gln Pro Arg Glu Pro Gln Val Tyr
        355                 360                 365

Thr Leu Pro Pro Ser Arg Glu Glu Met Thr Lys Asn Gln Val Ser Leu
    370                 375                 380

Thr Cys Leu Val Lys Gly Phe Tyr Pro Ser Asp Ile Ala Val Glu Trp
385                 390                 395                 400

Glu Ser Asn Gly Gln Pro Glu Asn Asn Tyr Lys Thr Thr Pro Pro Met
                405                 410                 415

Leu Asp Ser Asp Gly Ser Phe Phe Leu Tyr Ser Lys Leu Thr Val Asp
            420                 425                 430

Lys Ser Arg Trp Gln Gln Gly Asn Val Phe Ser Cys Ser Val Met His
        435                 440                 445

Glu Ala Leu His Asn His Tyr Thr Gln Lys Ser Leu Ser Leu Ser Pro
    450                 455                 460

Gly Lys Gly Gly Gly Gly Ser Gly Gly Gly Ser Gln Val Gln Leu
465                 470                 475                 480
```

Val Gln Ser Gly Ala Glu Val Lys Lys Pro Gly Ala Ser Val Lys Leu
            485                 490                 495

Ser Cys Lys Ala Ser Gly Tyr Thr Phe Ser Ser Tyr Trp Met His Trp
        500                 505                 510

Val Arg Gln Ala Pro Gly Gln Gly Leu Glu Trp Ile Gly Glu Ile Asn
        515                 520                 525

Pro Gly Asn Gly His Thr Asn Tyr Asn Glu Lys Phe Lys Ser Arg Val
        530                 535                 540

Thr Met Thr Arg Asp Thr Ser Thr Ser Thr Ala Tyr Met Glu Leu Ser
545                 550                 555                 560

Ser Leu Arg Ser Glu Asp Thr Ala Val Tyr Tyr Cys Ala Arg Ser Phe
                565                 570                 575

Lys Thr Ala Arg Ala Phe Ala Tyr Trp Gly Gln Gly Thr Leu Val Thr
            580                 585                 590

Val Ser Ser Gly Gly Gly Gly Ser Gly Gly Gly Gly Ser Gly Gly Gly
        595                 600                 605

Gly Ser Asp Ile Val Met Thr Gln Ser Pro Ala Phe Leu Ser Val Thr
    610                 615                 620

Pro Gly Glu Lys Val Thr Ile Thr Cys Arg Ala Ser Gln Thr Ile Ser
625                 630                 635                 640

Asp Tyr Leu His Trp Tyr Gln Gln Lys Pro Asp Gln Ala Pro Lys Leu
                645                 650                 655

Leu Ile Lys Tyr Ala Ser Gln Ser Ile Ser Gly Ile Pro Ser Arg Phe
            660                 665                 670

Ser Gly Ser Gly Ser Gly Thr Asp Phe Thr Phe Thr Ile Ser Ser Leu
        675                 680                 685

Glu Ala Glu Asp Ala Ala Thr Tyr Tyr Cys Gln Asp Gly His Ser Trp
    690                 695                 700

Pro Pro Thr Phe Gly Gln Gly Thr Lys Leu Glu Ile Lys
705                 710                 715

<210> SEQ ID NO 6
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 6

Gly Gly Gly Gly Ser Gly Gly Gly Gly Ser
1               5                   10

<210> SEQ ID NO 7
<211> LENGTH: 15
<212> TYPE: PRT
<213> ORGANISM: Artificial Sequence
<220> FEATURE:
<223> OTHER INFORMATION: Synthetic Peptide

<400> SEQUENCE: 7

Gly Gly Gly Gly Ser Gly Gly Gly Gly Ser Gly Gly Gly Gly Ser
1               5                   10                  15

<210> SEQ ID NO 8
<211> LENGTH: 18
<212> TYPE: PRT
<213> ORGANISM: Artificial Sequence
<220> FEATURE:
<223> OTHER INFORMATION: Synthetic Peptide

```
<400> SEQUENCE: 8

Gly Ser Thr Ser Gly Ser Gly Lys Pro Gly Ser Gly Glu Gly Ser Thr
1               5                   10                  15

Lys Gly

<210> SEQ ID NO 9
<211> LENGTH: 19
<212> TYPE: PRT
<213> ORGANISM: Artificial Sequence
<220> FEATURE:
<223> OTHER INFORMATION: Synthetic Peptide

<400> SEQUENCE: 9

Gly Ser Thr Ser Gly Ser Gly Lys Pro Gly Ser Gly Glu Gly Ser Thr
1               5                   10                  15

Lys Gly Ser

<210> SEQ ID NO 10
<211> LENGTH: 120
<212> TYPE: PRT
<213> ORGANISM: Artificial Sequence
<220> FEATURE:
<223> OTHER INFORMATION: Synthetic Peptide

<400> SEQUENCE: 10

Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Cys Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 11
<211> LENGTH: 127
<212> TYPE: PRT
<213> ORGANISM: Artificial Sequence
<220> FEATURE:
<223> OTHER INFORMATION: Synthetic Peptide

<400> SEQUENCE: 11

Met Asp Ser Gln Ala Gln Val Leu Met Leu Leu Leu Leu Ser Val Ser
1               5                   10                  15

Gly Thr Cys Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
        50                  55                  60
```

```
Lys Leu Leu Ile Tyr Ser Ala Ser Phe Leu Tyr Ser Gly Val Pro Ser
 65                  70                  75                  80

Arg Phe Ser Gly Ser Arg Ser Gly Thr Asp Phe Thr Leu Thr Ile Ser
                 85                  90                  95

Ser Leu Gln Pro Glu Asp Phe Ala Thr Tyr Tyr Cys Gln Gln His Tyr
            100                 105                 110

Thr Thr Pro Pro Thr Phe Gly Cys Gly Thr Lys Val Glu Ile Lys
        115                 120                 125

<210> SEQ ID NO 12
<211> LENGTH: 329
<212> TYPE: PRT
<213> ORGANISM: Artificial Sequence
<220> FEATURE:
<223> OTHER INFORMATION: Synthetic Peptide

<400> SEQUENCE: 12

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
    130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300
```

```
Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 13
<211> LENGTH: 234
<212> TYPE: PRT
<213> ORGANISM: Artificial Sequence
<220> FEATURE:
<223> OTHER INFORMATION: Synthetic Peptide

<400> SEQUENCE: 13

Met Asp Ser Gln Ala Gln Val Leu Met Leu Leu Leu Ser Val Ser
1               5                   10                  15

Gly Thr Cys Gly Asp Ile Gln Met Thr Gln Ser Pro Ser Ser Leu Ser
                20                  25                  30

Ala Ser Val Gly Asp Arg Val Thr Ile Thr Cys Arg Ala Ser Gln Asp
            35                  40                  45

Val Asn Thr Ala Val Ala Trp Tyr Gln Gln Lys Pro Gly Lys Ala Pro
    50                  55                  60

Lys Leu Leu Ile Tyr Ser Ala Ser Phe Leu Tyr Ser Gly Val Pro Ser
65                  70                  75                  80

Arg Phe Ser Gly Ser Arg Ser Gly Thr Asp Phe Thr Leu Thr Ile Ser
                85                  90                  95

Ser Leu Gln Pro Glu Asp Phe Ala Thr Tyr Tyr Cys Gln Gln His Tyr
            100                 105                 110

Thr Thr Pro Pro Thr Phe Gly Gln Gly Thr Lys Val Glu Ile Lys Arg
            115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
            195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230
```

ANTI-HER2/ANTI-4-1BB BISPECIFIC ANTIBODIES AND USES THEREOF

CROSS-REFERENCE TO RELATED APPLICATIONS

The present application claims priority to U.S. 63/062,697, filed Aug. 7, 2020, the entire contents of which are incorporated herein by reference.

BACKGROUND OF THE INVENTION

Field of the Invention

The present invention provides a bispecific antibody that more potently induces activated T cells dependent on HER2 expression.

Discussion of the Background

Cancer remains one of the leading causes of death in the world. Recent statistics report that 13% of the world population dies from cancer. According to estimates from the International Agency for Research on Cancer (IARC), in 2012 there were 14.1 million new cancer cases and 8.2 million cancer deaths worldwide. By 2030, the global burden is expected to grow to 21.7 million new cancer cases and 13 million cancer deaths due to population growth and aging and exposure to risk factors such as smoking, unhealthy diet and physical inactivity. Further, pain and medical expenses for cancer treatment cause reduced quality of life for both cancer patients and their families.

SUMMARY OF THE INVENTION

Provided herein is a bispecific epitope binding protein. The epitope binding protein is a multimer of four single-chain chimeric polypeptide chains, two heavy chains and two light chains. The bispecific epitope binding protein comprises: (a) a first antigen binding domain and (b) a second antigen binding domain, wherein the first antigen binding domain binds specifically to HER2 and the second antigen binding domain binds specifically to 4-1BB.

In some embodiments, in the bispecific epitope binding protein,
  each single-chain chimeric heavy chain comprises an antibody variable region and scFv linked to CH1/Fc, and
  each single-chain chimeric light chain comprises an antibody variable region linked to a C kappa region,
  wherein the first antigen binding domain is formed by the antibody variable region of the single-chain chimeric heavy chain and the antibody variable region of the single-chain chimeric light chain, and
  wherein the second antigen binding domain is formed by the scFv.

In some embodiments, the heavy single-chain chimeric polypeptide of bispecific epitope binding protein comprises a first linker sequence. In some embodiments, the first linker sequence is between the first antigen binding domain and the second antigen binding domain. In some embodiments, the first linker sequence comprises a $(G_4S)_2$ or a 218S linker. In some embodiments, the first linker sequence comprises a $(G_4S)_2$ linker.

In some embodiments, the first antigen binding domain comprises an antibody. In some embodiments, the first antigen binding domain comprises a human or humanized antibody.

In some embodiments, the second antigen binding domain comprises a scFv. In some embodiments, the second antigen binding domain further comprises a second linker sequence between the variable region of the heavy ($V_H$) and light chains ($V_L$) of immunoglobulin chains. In some embodiments, the second linker sequence comprises a $(G_4S)_3$ or a 218 linker. In some embodiments, the second linker sequence comprises a $(G_4S)_3$ linker.

In some embodiments, the first antigen binding domain or antigen-binding antibody fragment includes substantial homology to an antibody or antibody fragment that includes a heavy chain variable domain that is or includes a sequence selected from SEQ ID NOs: 1 and 10, respectively and a light chain variable domain or antigen-binding antibody fragment that includes a sequence of SEQ ID NO: 2 and 11 respectively. In some embodiments, the first antigen binding domain or antigen-binding antibody fragment includes a heavy chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence selected from SEQ ID NOs: 1 and 10, respectively and a light chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence of SEQ ID NO: 2 and 11, respectively. In some embodiments, the first antigen binding domain or antigen-binding antibody fragment includes a heavy chain variable domain that is or includes a sequence selected from SEQ ID NOs: 1 and 10, respectively and a light chain variable domain that is or includes a sequence of SEQ ID NO: 2 and 11, respectively.

In some embodiments, the first linker sequence comprises a sequence that is at least 80% identical to SEQ ID NO: 6 or 9. In some embodiments, the first linker sequence comprises a sequence that is at least 90% identical to SEQ ID NO: 6 or 9. In some embodiments, the first linker sequence comprises a sequence that is at least 95% identical to SEQ ID NO: 6 or 9. In some embodiments, the first linker sequence comprises a sequence that is at least 98% identical to SEQ ID NO: 6 or 9. In some embodiments, the first linker sequence comprises SEQ ID NO: 6 or 9.

In some embodiments, the second antigen binding domain or antigen-binding antibody fragment includes substantial homology to an antibody or antibody fragment that includes a heavy chain variable domain that is or includes a sequence selected from SEQ ID NOs: 3 and a light chain variable domain or antigen-binding antibody fragment that include a sequence of SEQ ID NO: 4. In some embodiments, the second antigen binding domain or antigen-binding antibody fragment includes a heavy chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence selected from SEQ ID NOs: 3 and a light chain variable domain that is or includes a sequence at least 90%, 91%, 92%, 93%, 94%, 95%, 96%, 97%, 98%, 99%, 99.1%, 99.2%, 99.3%, 99.4% or 99.5% identical to a sequence of SEQ ID NO: 4. In some embodiments, the second antigen binding domain or antigen-binding antibody fragment includes a heavy chain variable domain that is or includes a sequence selected from SEQ ID NOs: 3 and a light chain variable domain that is or includes a sequence of SEQ ID NO: 4.

In some embodiments, the second linker sequence comprises a sequence that is at least 80% identical to SEQ ID NO: 7 or 8. In some embodiments, the second linker sequence comprises a sequence that is at least 90% identical to SEQ ID NO: 7 or 8. In some embodiments, the second linker sequence comprises a sequence that is at least 95% identical to SEQ ID NO: 7 or 8. In some embodiments, the second linker sequence comprises a sequence that is at least 98% identical to SEQ ID NO: 7 or 8. In some embodiments, the second linker sequence comprises SEQ ID NO: 7 or 8.

In some embodiments, a provided antigen binding domain or fragment is or comprises a humanized antibody. In some embodiments, a provided the first antigen binding domain or the second binding domain includes a human immunoglobulin constant domain, wherein the constant domain is selected from an IgG1 or a variant thereof, an IgG2 or a variant thereof, an IgG4 or a variant thereof, as well as humanized IgG1/2 or a variant thereof. In some embodiments, a provided antigen binding domain or fragment thereof is or comprises a human IgG1/2 hybrid. In some embodiments, an IgG1/2 is or comprises a sequence that is at least 95% identical to SEQ ID NO: 12

Provided herein are pharmaceutical compositions comprising: bispecific epitope binding protein and multimer of single-chain chimeric polypeptides described herein, any one of the nucleic acid molecules described herein, any one of the recombinant vectors described herein, or any one of the cells described herein; and a pharmaceutically acceptable carrier.

Provided herein are kits comprising any one of the pharmaceutical compositions described herein.

Provided herein are methods of producing a bispecific epitope binding protein, the method comprising: culturing any one of the cells described herein in a culture medium under conditions sufficient to result in the production of the bispecific epitope binding protein; and recovering the bispecific epitope binding protein from the cell and/or the culture medium.

Provided herein are methods of treating a subject in need thereof, the method comprising: administering to the subject a composition that comprises or delivers any one of the bispecific epitope binding proteins described herein, any one of the nucleic acid molecules described herein, any one of the recombinant vectors described herein, or any one of the cells described herein, thereby treating a disease or a condition. In some embodiments, the subject has, or is at risk for developing, cancer. In some embodiments, the cancer comprises a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, prostate cancer, and combinations thereof.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

FIG. 4A, FIG. 4B, and FIG. 4C show cell lines profile for binding assay.

DETAILED DESCRIPTION OF THE INVENTION

Figures 1A, 1B:
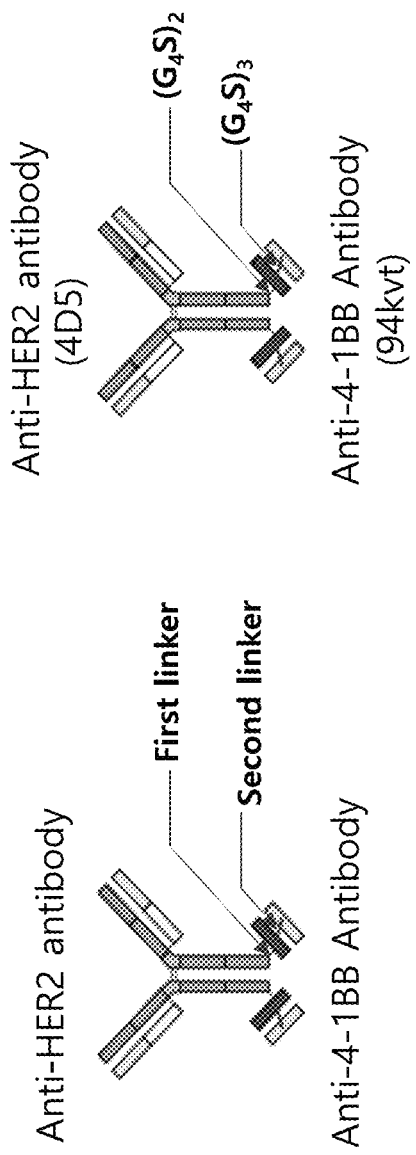
FIG. 1A shows the structure of anti-Her2/anti-4-1BB bispecific antibody
FIG. 1B shows the structure of 4D5×94 kvt

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

This disclosure describes a bispecific epitope binding protein. The epitope binding protein is a multimer of four single-chain chimeric polypeptide chains, two heavy chains and two light chains. The bispecific epitope binding protein comprises: (a) a first antigen binding domain and (b) a second antigen binding domain, wherein the first antigen binding domain binds specifically to HER2 and the second antigen binding domain binds specifically to 4-1BB.

Definitions

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that are within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Administration: As used herein, the term "administration" typically refers to the administration of a composition to a subject or system to achieve delivery of an agent that is, or is included in, the composition. Those of ordinary skill in the art will be aware of a variety of routes that may, in appropriate circumstances, be utilized for administration to a subject, for example a human. For example, in some embodiments, administration may be ocular, oral, parenteral, topical, etc. In some particular embodiments, administration may be bronchial (e.g., by bronchial instillation), buccal, dermal (which may be or comprise, for example, one or more of topical to the dermis, intradermal, interdermal, transdermal, etc.), enteral, intra-arterial, intradermal, intragastric, intramedullary, intramuscular, intranasal, intraperitoneal, intrathecal, intravenous, intraventricular, within a specific organ (e. g. intrahepatic), mucosal, nasal, oral, rectal, subcutaneous, sublingual, topical, tracheal (e.g., by intratracheal instillation), vaginal, vitreal, etc. In some embodiments, administration may involve only a single dose. In some embodiments, administration may involve application of a fixed number of doses. In some embodiments, administration may involve dosing that is intermittent (e.g., a plurality of doses separated in time) and/or periodic (e.g., individual doses separated by a common period of time) dosing. In some embodiments, administration may involve continuous dosing (e.g., perfusion) for at least a selected period of time.

Affinity: As is known in the art, "affinity" is a measure of the strength a particular ligand binds to its partner. Affinities can be measured in different ways. In some embodiments, affinity is measured by a quantitative assay. In some such embodiments, binding partner concentration may be fixed to be in excess of ligand concentration so as to mimic physiological conditions. Alternatively or additionally, in some embodiments, binding partner concentration and/or ligand concentration may be varied. In some such embodiments, affinity may be compared to a reference under comparable conditions (e.g., concentrations).

Antibody: As used herein, the term "antibody" refers to an immunoglobulin molecule that includes one or more antigen-binding domains that specifically bind to a particular antigen. In some embodiments, the term encompasses any polypeptide or polypeptide complex that includes immunoglobulin structural elements sufficient to confer specific binding.

Exemplary antibodies include, but are not limited to monoclonal antibodies, polyclonal antibodies, and fragments thereof. In some embodiments, an antibody may include one or more sequence elements are humanized, primatized, chimeric, etc., as is known in the art. In many embodiments, the term "antibody" is used to refer to one or more of the art-known or developed constructs or formats for utilizing antibody structural and functional features in alternative presentation. For example, embodiments, an antibody utilized in accordance with the present invention is in a format selected from, but not limited to, intact IgA, IgG, IgE, or IgM antibodies; bi- or multi-specific antibodies (e.g., Zybodies®, etc.); antibody fragments such as Fab fragments, Fab' fragments, F(ab')2 fragments, Fd' fragments, Fd fragments, and isolated CDRs or sets thereof single chain Fvs; polypeptide-Fc fusions; single domain antibodies (e.g., shark single domain antibodies such as IgNAR or fragments thereof); cameloid antibodies; masked antibodies (e.g., Probodies®); Small Modular ImmunoPharmaceuticals ("SMIPs™"); single chain or Tandem diabodies (TandAb®); VHHs; Anticalins®; Nanobodies® minibodies; BiTE®s; ankyrin repeat proteins or DARPINs®; Avimers®; DARTs; TCR-like antibodies; Adnectins®; Affilins®; Transbodies®; Affibodies®; TrimerX®; MicroProteins; Fynomers®, Centyrins®; and KALBITOR®s. In some embodiments, an antibody may lack a covalent modification (e.g., attachment of a glycan) that it would have if produced naturally. In some embodiments, an antibody may contain a covalent modification (e.g., attachment of a glycan, a payload [e.g., a detectable moiety, a therapeutic moiety, a catalytic moiety, etc.], or other pendant group [e.g., polyethylene glycol, etc.]. In many embodiments, an antibody is or comprises a polypeptide whose amino acid sequence includes one or more structural elements recognized by those skilled in the art as a complementarity determining region (CDR); in some embodiments an antibody is or comprises a polypeptide whose amino acid sequence includes at least one CDR (e.g., at least one heavy chain CDR and/or at least one light chain CDR) that is substantially identical to one found in a reference antibody. In some embodiments an included CDR is substantially identical to a reference CDR in that it is either identical in sequence or contains between 1-5 amino acid substitutions as compared with the reference CDR. In some embodiments an included CDR is substantially identical to a reference CDR in that it shows at least 85%, 86%, 87%, 88%, 89%, 90%, 91%, 92%, 93%, 94%, 95%, 96%, 97%, 98%, 99%, or 100% sequence identity with the reference CDR. In some embodiments an included CDR is substantially identical to a reference CDR in that it shows at least 96%, 96%, 97%, 98%, 99%, or 100% sequence identity with the reference CDR. In some embodiments an included CDR is substantially identical to a reference CDR in that at least one amino acid within the included CDR is deleted, added, or substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments an included CDR is substantially identical to a reference CDR in that at least one amino acid within the included CDR is substituted as compared with the reference CDR but the included CDR has an amino acid sequence that is otherwise identical with that of the reference CDR. In some embodiments an included CDR is substantially identical to a reference CDR in that 1-5 amino acids within the included CDR are deleted, added, or substituted as compared with the reference CDR but the included CDR has an amino acid sequence that is otherwise identical to the reference CDR. In some embodiments, an antibody is or comprises a polypeptide whose amino acid sequence includes structural elements recognized by those skilled in the art as an immunoglobulin variable domain. In some embodiments, an antibody is a polypeptide protein having a binding domain which is homologous or largely homologous to an immunoglobulin-binding domain. In some embodiments, an antibody is or comprises at least a portion of a chimeric antigen receptor (CAR).

Antigen: The term "antigen", as used herein, refers to an agent that binds to an antibody agent. In some embodiments, an antigen binds to an antibody agent and may or may not induce a particular physiological response in an organism. In general, an antigen may be or include any chemical entity such as, for example, a small molecule, a nucleic acid, a polypeptide, a carbohydrate, a lipid, a polymer (including biologic polymers [e.g., nucleic acid and/or amino acid polymers] and polymers other than biologic polymers [e.g., other than a nucleic acid or amino acid polymer]) etc. In some embodiments, an antigen is or comprises a polypeptide. In some embodiments, an antigen is or comprises a glycan. Those of ordinary skill in the art will appreciate that, in general, an antigen may be provided in isolated or pure form, or alternatively may be provided in crude form (e.g., together with other materials, for example in an extract such as a cellular extract or other relatively crude preparation of an antigen-containing source).

In some certain embodiments, an antigen is present in a cellular context (e.g., an antigen is expressed on the surface of a cell or expressed in a cell). In some embodiments, an antigen is a recombinant antigen.

Antigen binding domain: As used herein, can refer to an antibody agent or portion thereof that specifically binds to a target moiety or entity. Typically, the interaction between an antigen binding domain and its target is non-covalent. In some embodiments, a target moiety or entity can be of any chemical class including, for example, a carbohydrate, a lipid, a nucleic acid, a metal, a polypeptide, or a small molecule. In some embodiments, an antigen binding domain may be or comprise a polypeptide (or complex thereof). In some embodiments, an antigen binding domain is part of a fusion polypeptide. In some embodiments, an antigen binding domain is part of a chimeric antigen receptor (CAR).

Associated with: Two events or entities are "associated" with one another, as that term is used herein, if the presence, level, and/or form of one is correlated with that of the other. For example, a particular entity (e.g., polypeptide, genetic signature, metabolite, microbe, etc.) is considered to be associated with a particular disease, disorder, or condition, if its presence, level and/or form correlates with incidence of and/or susceptibility to the disease, disorder, or condition (e.g., across a relevant population). In some embodiments, two or more entities are physically "associated" with one another if they interact, directly or indirectly, so that they are and/or remain in physical proximity with one another. In some embodiments, two or more entities that are physically associated with one another are covalently linked to one another; in some embodiments, two or more entities that are physically associated with one another are not covalently linked to one another but are non-covalently associated, for example by means of hydrogen bonds, van der Waals interaction, hydrophobic interactions, magnetism, and combinations thereof.

Binding: It will be understood that the term "binding", as used herein, typically refers to a non-covalent association between or among two or more entities. "Direct" binding involves physical contact between entities or moieties; indirect binding involves physical interaction by way of physical contact with one or more intermediate entities. Binding between two or more entities can typically be assessed in any of a variety of contexts—including where interacting entities or moieties are studied in isolation or in the context of more complex systems (e.g., while covalently or otherwise associated with a carrier entity and/or in a biological system or cell).

Cancer: The terms "cancer", "malignancy", "neoplasm", "tumor", and "carcinoma", are used herein to refer to cells that exhibit relatively abnormal, uncontrolled, and/or autonomous growth, so that they exhibit an aberrant growth phenotype characterized by a significant loss of control of cell proliferation. In some embodiments, a tumor may be or comprise cells that are precancerous (e.g., benign), malignant, pre-metastatic, metastatic, and/or non-metastatic. The present disclosure specifically identifies certain cancers to which its teachings may be particularly relevant. In some embodiments, a relevant cancer may be characterized by a solid tumor. In some embodiments, a relevant cancer may be characterized by a hematologic tumor. In general, examples of different types of cancers known in the art include, for example, hematopoietic cancers including leukemias, lymphomas (Hodgkin's and non-Hodgkin's), myelomas and myeloproliferative disorders; sarcomas, melanomas, adenomas, carcinomas of solid tissue, squamous cell carcinomas of the mouth, throat, larynx, and lung, liver cancer, genitourinary cancers such as prostate, cervical, bladder, uterine, and endometrial cancer and renal cell carcinomas, bone cancer, pancreatic cancer, skin cancer, cutaneous or intraocular melanoma, cancer of the endocrine system, cancer of the thyroid gland, cancer of the parathyroid gland, head and neck cancers, breast cancer, gastro-intestinal cancers and nervous system cancers, benign lesions such as papillomas, and the like.

Chemotherapeutic Agent: The term "chemotherapeutic agent", has used herein has its art-understood meaning referring to one or more pro-apoptotic, cytostatic and/or cytotoxic agents, for example specifically including agents utilized and/or recommended for use in treating one or more diseases, disorders or conditions associated with undesirable cell proliferation. In many embodiments, chemotherapeutic agents are useful in the treatment of cancer. In some embodiments, a chemotherapeutic agent may be or comprise one or more alkylating agents, one or more anthracyclines, one or more cytoskeletal disruptors (e.g. microtubule targeting agents such as taxanes, maytansine and analogs thereof, of), one or more epothilones, one or more histone deacetylase inhibitors HDACs), one or more topoisomerase inhibitors (e.g., inhibitors of topoisomerase I and/or topoisomerase II), one or more kinase inhibitors, one or more nucleotide analogs or nucleotide precursor analogs, one or more peptide antibiotics, one or more platinum-based agents, one or more retinoids, one or more vinca alkaloids, and/or one or more analogs of one or more of the following (i.e., that share a relevant anti-proliferative activity). In some particular embodiments, a chemotherapeutic agent may be or comprise one or more of Actinomycin, All-trans retinoic acid, an Auiristatin, Azacitidine, Azathioprine, Bleomycin, Bortezomib, Carboplatin, Capecitabine, Cisplatin, Chlorambucil, Cyclophosphamide, Curcumin, Cytarabine, Daunorubicin, Docetaxel, Doxifluridine, Doxorubicin, Epirubicin, Epothilone, Etoposide, Fluorouracil, Gemcitabine, Hydroxyurea, Idarubicin, Imatinib, Irinotecan, Maytansine and/or analogs thereof (e.g. DM1) Mechlorethamine, Mercaptopurine, Methotrexate, Mitoxantrone, a Maytansinoid, Oxaliplatin, Paclitaxel, Pemetrexed, Teniposide, Tioguanine, Topotecan, Valrubicin, Vinblastine, Vincristine, Vindesine, Vinorelbine, and combinations thereof. In some embodiments, a chemotherapeutic agent may be utilized in the context of an antibody-drug conjugate. In some embodiments, a chemotherapeutic agent is one found in an antibody-drug conjugate selected from the group consisting of: hLL1-doxorubicin, hRS7-SN-38, hMN-14-SN-38, hLL2-SN-38, hA20-SN-38, hPAM4-SN-38, hLL1-SN-38, hRS7-Pro-2-P-Dox, hMN-14-Pro-2-P-Dox, hLL2-Pro-2-P-Dox, hA20-Pro-2-P-Dox, hPAM4-Pro-2-P-Dox, hLL1-Pro-2-P-Dox, P4/D10-doxorubicin, gemtuzumab ozogamicin, brentuximab vedotin, trastuzumab emtansine, inotuzumab ozogamicin, glembatumomab vedotin, SAR3419, SAR566658, BIIB015, BT062, SGN-75, SGN-CD19A, AMG-172, AMG-595, BAY-94-9343, ASG-SME, ASG-22ME, ASG-16M8F, MDX-1203, MLN-0264, anti-PSMA ADC, RG-7450, RG-7458, RG-7593, RG-7596, RG-7598, RG-7599, RG-7600, RG-7636, ABT-414, IMGN-853, IMGN-529, vorsetuzumab mafodotin, and lorvotuzumab mertansine.

Engineered: In general, the term "engineered" refers to the aspect of having been manipulated by the hand of man. For example, a polypeptide is considered to be "engineered" when the polypeptide sequence manipulated by the hand of man. For example, in some embodiments of the present invention, an engineered polypeptide comprises a sequence that includes one or more amino acid mutations, deletions and/or insertions that have been introduced by the hand of man into a reference polypeptide sequence. In some embodiments, an engineered polypeptide includes a polypeptide that has been fused (i.e., covalently linked) to one or more additional polypeptides by the hand of man, to form a fusion polypeptide that would not naturally occur in vivo. Comparably, a cell or organism is considered to be "engineered" if it has been manipulated so that its genetic information is altered (e.g., new genetic material not previously present has been introduced, for example by transformation, mating, somatic hybridization, transfection, transduction, or other mechanism, or previously present genetic material is altered or removed, for example by substitution or deletion mutation, or by mating protocols). As is common practice and is understood by those in the art, derivatives and/or progeny of an engineered polypeptide or cell are typically still referred to as "engineered" even though the actual manipulation was performed on a prior entity.

Pharmaceutical composition: As used herein, the term "pharmaceutical composition" refers to a composition in which an active agent is formulated together with one or more pharmaceutically acceptable carriers. In some embodiments, the composition is suitable for administration to a human or animal subject. In some embodiments, the active agent is present in unit dose amount appropriate for administration in a therapeutic regimen that shows a statistically significant probability of achieving a predetermined therapeutic effect when administered to a relevant population.

Pharmaceutically acceptable carrier: The term "pharmaceutically acceptable carrier", as used herein, generally has its art-recognized meaning of a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. The term "pharmaceutically acceptable carrier" may further include a pharmaceutically acceptable salt of the compound useful within the invention. Other additional ingredients that may be included in the pharmaceutical compositions used in the practice of the invention are described, for example, in Remington's Pharmaceutical Sciences (Genaro, Ed., Mack Publishing Co., 1985, Easton, Pa.), which is incorporated herein by reference. The "pharmaceutically acceptable carrier" is useful for the preparation of a pharmaceutical composition that is: generally compatible with the other ingredients of the composition, not deleterious to the recipient, and neither biologically nor otherwise undesirable. "A pharmaceutically acceptable carrier" includes one or more than one carrier. Embodiments include carriers for topical, ocular, parenteral, intravenous, intraperitoneal intramuscular, sublingual, nasal or oral administration. "Pharmaceutically acceptable carrier" also includes agents for preparation of aqueous dispersions and sterile powders for injection or dispersions.

Pharmaceutically acceptable salt: As used herein, the term "pharmaceutically acceptable salt" generally has its art-recognized meaning and refers to derivatives of the compounds provided herein wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the compounds provided herein include the conventional non-toxic salts of the parent compound formed, for example, from non-toxic inorganic or organic acids. The pharmaceutically acceptable salts of the compounds provided herein can be synthesized from the parent compound which contains a basic or acidic moiety by conventional chemical methods. Generally, such salts can be prepared by combining the free acid or base forms of these compounds with a stoichiometric amount of the appropriate base or acid in water or in an organic solvent, or in a mixture of the two; generally, nonaqueous media such as ether, ethyl acetate, ethanol, isopropanol, or acetonitrile may be used. Lists of suitable salts are found in Remington's Pharmaceutical Sciences, 17th ed., Mack Publishing Company, Easton, Pa., 1985, p. 1418 and Journal of Pharmaceutical Science, 66, 2 (1977), each of which is incorporated herein by reference in its entirety.

Excipient: As used herein, the term "excipient" generally has its art-recognized meaning and refers to physiologically compatible additives useful in preparation of a pharmaceutical composition. Examples of pharmaceutically acceptable carriers and excipients can, for example, be found in Remington Pharmaceutical Science, 16th Ed.

Polypeptide: The term "polypeptide", as used herein, generally has its art—recognized meaning of a polymer of at least three amino acids. Those of ordinary skill in the art will appreciate that the term "polypeptide" is intended to be sufficiently general as to encompass not only polypeptides having a complete sequence recited herein, but also to encompass polypeptides that represent functional fragments (i.e., fragments retaining at least one activity) of such complete polypeptides. Moreover, those of ordinary skill in the art understand that protein sequences generally tolerate some substitution without destroying activity. Thus, any polypeptide that retains activity and shares at least about 30-40% overall sequence identity, often greater than about 50%, 60%, 70%, or 80%, and further usually including at least one region of much higher identity, often greater than 90% or even 95%, 96%, 97%, 98%, or 99% in one or more highly conserved regions, usually encompassing at least 3-4 and often up to 20 or more amino acids, with another polypeptide of the same class, is encompassed within the relevant term "polypeptide" as used herein. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibody agents, antibody fragments, biologically active portions thereof, and/or characteristic portions thereof.

Recombinant: as used herein, is intended to refer to polypeptides that are designed, engineered, prepared, expressed, created, manufactured, and/or or isolated by recombinant means, such as polypeptides expressed using a recombinant expression vector transfected into a host cell; polypeptides isolated from a recombinant, combinatorial human polypeptide library; polypeptides isolated from an animal (e.g., a mouse, rabbit, sheep, fish, etc.) that is transgenic for or otherwise has been manipulated to express a gene or genes, or gene components that encode and/or direct expression of the polypeptide or one or more component(s), portion(s), element(s), or domain(s) thereof; and/or polypeptides prepared, expressed, created or isolated by any other means that involves splicing or ligating selected nucleic acid sequence elements to one another, chemically synthesizing selected sequence elements, and/or otherwise generating a nucleic acid that encodes and/or directs expression of the polypeptide or one or more component(s), portion(s), element(s), or domain(s) thereof. In some embodiments, one or more of such selected sequence elements is found in nature. In some embodiments, one or more of such selected sequence elements is designed in silico. In some embodiments, one or more such selected sequence elements results from mutagenesis (e.g., in vivo or in vitro) of a known sequence element, e.g., from a natural or synthetic source such as, for example, in the germline of a source organism of interest (e.g., of a human, a mouse, etc.).

Specific binding: As used herein, the term "specific binding" refers to an ability to discriminate between possible binding partners in the environment in which binding is to occur. A binding agent that interacts with one particular target when other potential targets are present is said to "bind specifically" to the target with which it interacts. In some embodiments, specific binding is assessed by detecting or determining degree of association between the binding agent and its partner; in some embodiments, specific binding is assessed by detecting or determining degree of dissociation of a binding agent-partner complex; in some embodiments, specific binding is assessed by detecting or determining ability of the binding agent to compete an alternative interaction between its partner and another entity. In some embodiments, specific binding is assessed by performing such detections or determinations across a range of concentrations.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Therapeutic agent: As used herein, the phrase "therapeutic agent" in general refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is a substance that can be used to alleviate, ameliorate, relieve, inhibit, prevent, delay onset of, reduce severity of, and/or reduce incidence of one or more symptoms or features of a disease, disorder, and/or condition. In some embodiments, a "therapeutic agent" is an agent that has been or is required to be approved by a government agency before it can be marketed for administration to humans. In some embodiments, a "therapeutic agent" is an agent for which a medical prescription is required for administration to humans.

Therapeutically Effective Amount: As used herein, the term "therapeutically effective amount" means an amount that is sufficient, when administered to a population suffering from or susceptible to a disease, disorder, and/or condition in accordance with a therapeutic dosing regimen, to treat the disease, disorder, and/or condition. In some embodiments, a therapeutically effective amount is one that reduces the incidence and/or severity of, stabilizes one or more characteristics of, and/or delays onset of, one or more symptoms of the disease, disorder, and/or condition. Those of ordinary skill in the art will appreciate that the term "therapeutically effective amount" does not in fact require successful treatment be achieved in a particular individual. Rather, a therapeutically effective amount may be that amount that provides a particular desired pharmacological response in a significant number of subjects when administered to patients in need of such treatment. For example, in some embodiments, term "therapeutically effective amount", refers to an amount which, when administered to an individual in need thereof in the context of inventive therapy, will block, stabilize, attenuate, or reverse a cancer-supportive process occurring in said individual, or will enhance or increase a cancer-suppressive process in said individual. In the context of cancer treatment, a "therapeutically effective amount" is an amount which, when administered to an individual diagnosed with a cancer, will prevent, stabilize, inhibit, or reduce the further development of cancer in the individual. A particularly preferred "therapeutically effective amount" of a composition described herein reverses (in a therapeutic treatment) the development of a malignancy such as a pancreatic carcinoma or helps achieve or prolong remission of a malignancy. A therapeutically effective amount administered to an individual to treat a cancer in that individual may be the same or different from a therapeutically effective amount administered to promote remission or inhibit metastasis. As with most cancer therapies, the therapeutic methods described herein are not to be interpreted as, restricted to, or otherwise limited to a "cure" for cancer; rather the methods of treatment are directed to the use of the described compositions to "treat" a cancer, i.e., to effect a desirable or beneficial change in the health of an individual who has cancer. Such benefits are recognized by skilled healthcare providers in the field of oncology and include, but are not limited to, a stabilization of patient condition, a decrease in tumor size (tumor regression), an improvement in vital functions (e.g., improved function of cancerous tissues or organs), a decrease or inhibition of further metastasis, a decrease in opportunistic infections, an increased survivability, a decrease in pain, improved motor function, improved cognitive function, improved feeling of energy (vitality, decreased malaise), improved feeling of well-being, restoration of normal appetite, restoration of healthy weight gain, and combinations thereof. In addition, regression of a particular tumor in an individual (e.g., as the result of treatments described herein) may also be assessed by taking samples of cancer cells from the site of a tumor such as a pancreatic adenocarcinoma (e.g., over the course of treatment) and testing the cancer cells for the level of metabolic and signaling markers to monitor the status of the cancer cells to verify at the molecular level the regression of the cancer cells to a less malignant phenotype. For example, tumor regression induced by employing the methods of this invention would be indicated by finding a decrease in any of the pro-angiogenic markers discussed above, an increase in anti-angiogenic markers described herein, the normalization (i.e., alteration toward a state found in normal individuals not suffering from cancer) of metabolic pathways, intercellular signaling pathways, or intracellular signaling pathways that exhibit abnormal activity in individuals diagnosed with cancer. Those of ordinary skill in the art will appreciate that, in some embodiments, a therapeutically effective amount may be formulated and/or administered in a single dose. In some embodiments, a therapeutically effective amount may be formulated and/or administered in a plurality of doses, for example, as part of a dosing regimen.

Variant: As used herein in the context of molecules, e.g., nucleic acids, proteins, or small molecules, the term "variant" refers to a molecule that shows significant structural identity with a reference molecule but differs structurally from the reference molecule, e.g., in the presence or absence or in the level of one or more chemical moieties as compared to the reference entity. In some embodiments, a variant also differs functionally from its reference molecule. In general, whether a particular molecule is properly considered to be a "variant" of a reference molecule is based on its degree of structural identity with the reference molecule. As will be appreciated by those skilled in the art, any biological or chemical reference molecule has certain characteristic structural elements. A variant, by definition, is a distinct molecule that shares one or more such characteristic structural elements but differs in at least one aspect from the reference molecule. To give but a few examples, a polypeptide may have a characteristic sequence element comprised of a plurality of amino acids having designated positions relative to one another in linear or three-dimensional space and/or contributing to a particular structural motif and/or biological function; a nucleic acid may have a characteristic sequence element comprised of a plurality of nucleotide residues having designated positions relative to on another in linear or three-dimensional space. In some embodiments, a variant polypeptide or nucleic acid may differ from a reference polypeptide or nucleic acid as a result of one or more differences in amino acid or nucleotide sequence. In some embodiments, a variant polypeptide or nucleic acid shows an overall sequence identity with a reference polypeptide or nucleic acid that is at least 80%, 85%, 86%, 87%, 88%, 89%, 90%, 91%, 92%, 93%, 94%, 95%, 96%, 97%, or 99%. In some embodiments, a variant polypeptide or nucleic acid does not share at least one characteristic sequence element with a reference polypeptide or nucleic acid. In some embodiments, a reference polypeptide or nucleic acid has one or more biological activities. In some embodiments, a variant polypeptide or nucleic acid shares one or more of the biological activities of the reference polypeptide or nucleic acid.

Vector: as used herein, refers to a nucleic acid molecule capable of transporting another nucleic acid to which it has been linked. One type of vector is a "plasmid", which refers to a circular double stranded DNA loop into which additional DNA segments may be ligated.

Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "expression vectors." Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., *Molecular Cloning: A Laboratory Manual* 2nd ed., Cold Spring Harbor Laboratory Press, Cold Spring Harbor, N.Y. (1989)), which is incorporated herein by reference for any purpose.

"Single-Chain Chimeric" Polypeptide

As used herein, the term "single-chain chimeric" polypeptide refers to a single protein chain that includes amino acid sequences (e.g., domains) derived from two different sources (e.g., two different naturally-occurring proteins). In some embodiments, a single-chain chimeric polypeptide includes domains from at least two different naturally-occurring human proteins. In some embodiments, a single-chain chimeric polypeptide includes a domain that is a synthetic sequence (e.g., a scFv) and a domain that is derived from a naturally-occurring protein (e.g., a naturally-occurring human protein). In some embodiments, a single-chain chimeric polypeptide includes at least two different domains that are synthetic sequences (e.g., two different scFvs).

Bispecific Epitope Binding Protein

As used herein, a "bispecific epitope binding protein" refers to a protein that has two different antigen-binding specificities. In some embodiments, a bispecific epitope binding protein specifically binds to HER2 and 4-1BB. In some embodiments, the bispecific epitope binding protein comprises a full length antibody or an antibody fragment. In some embodiments, the bispecific epitope binding protein comprises a single chain Fv (scFv). In some embodiments, the bispecific epitope binding protein can be from a single species. In some embodiments the bispecific epitope binding protein can be chimerized or humanized.

In some embodiments, a bispecific epitope binding protein is provided. The epitope binding protein is a multimer of four single-chain chimeric polypeptide chains, two heavy chains and two light chains. The bispecific epitope binding protein comprises: (a) a first antigen binding domain and (b) a second antigen binding domain, wherein the first antigen binding domain binds specifically to HER2 and the second antigen binding domain binds specifically to 4-1BB.

Human Epidermal Growth Factor Receptor 2 (HER2)

HER2 (also referred to as CD340, ERBB2) is a member of the human epidermal growth factor receptor (HER/EGFR/ERBB) family. Members of the ERBB family of receptor tyrosine kinases are important mediators of cell growth, differentiation and survival. HER2 is a transmembrane surface-bound receptor tyrosine kinase and is normally involved in the signal transduction pathways leading to cell growth and differentiation.

Over-expression of HER2, the ERBB2 gene, occurs in approximately 15-30% of breast cancers and has been shown to play an important role in the development and progression of certain aggressive types of breast cancer. HER2 overexpression is also known to occur in ovarian, stomach, adenocarcinoma of the lung and aggressive forms of uterine cancer, such as uterine serous endometrial carcinoma.

In some embodiments, the first antigen binding domain or antigen-binding antibody fragment includes substantial homology to an antibody or antibody fragment that includes a heavy chain variable domain that is or includes a sequence selected from SEQ ID NOs: 1 and 10, respectively and a light chain variable domain or antigen-binding antibody fragment that includes a sequence of SEQ ID NO: 2 and 11 respectively. In some embodiments, the first antigen binding domain or antigen-binding antibody fragment includes a heavy chain variable domain that is or includes a sequence at least 80%, 85%, 90%, 91%, 92%, 93%, 94%, 95%, 96%, 97%, 98%, 99%, 99.1%, 99.2%, 99.3%, 99.4% or 99.5% identical to a sequence selected from SEQ ID NOs: 1 and 10, respectively. and a light chain variable domain that is or includes a sequence at least 80%, 85%, 90%, 91%, 92%, 93%, 94%, 95%, 96%, 97%, 98%, 99%, 99.1%, 99.2%, 99.3%, 99.4% or 99.5% identical to a sequence of SEQ ID NO: 2 and 11, respectively. In some embodiments, the first antigen binding domain or antigen-binding antibody fragment includes a heavy chain variable domain that is or includes a sequence selected from SEQ ID NOs: 1 and 10, respectively and a light chain variable domain that is or includes a sequence of SEQ ID NO: 2 and 11, respectively.

4-1BB 4-1BB (also referred to as CD137, TNFRSF9) is a receptor belonging to the tumor necrosis factor receptor (TNFR) superfamily. 4-1BB is a co-stimulatory molecule generally expressed in activated T lymphocytes and involved in immunity and autoimmune diseases (Kwon et al. PNAS 84: 2896, 1987; Kwon et al. PNAS 86: 1963, 1989; Son et al. Journal of Immunological Methods 286 (1-2): 187-201, 2004, each of which is herein incorporated by reference in its entirety). Human 4-1BB is a 255 amino acid protein and expressed on the cell surface in monomer (30 kDa) and dimer (55 kDa) forms and likely trimerizes with 4-1BB ligand to signal.

Further, 4-1BB is constitutively expressed on a number of cells, albeit at low levels, including Foxp3[+] Tregs and dendritic cells (DC). Activation with a number of agonists, such as cytokines (e.g., IL-2, IL-4), polyclonal activators (e.g., Con A and PHA), cell surface molecules (e.g., anti-CD3, anti-CD28) and promoters of $Ca^{2+}$ induction and PKC activity (e.g., ionomycin, photbol myristate acetate) further enhance expression of 4-1BB.

Numerous studies of murine and human T cells indicate that 4-1BB promotes enhanced cellular proliferation, survival, and cytokine production. Studies have indicated that some 4-1BB agonist monoclonal antibodies can increase costimulatory molecule expression and markedly enhance cytolytic T lymphocyte responses, resulting in anti-tumor efficacy in prophylactic and therapeutic settings. Further, 4-1BB monotherapy and combination therapy tumor models have established durable anti-tumor protective T cell memory responses. 4-1BB agonists also have been shown to inhibit autoimmune reactions in a variety of art-recognized autoimmunity models. This dual activity of 4-1BB offers the potential to provide anti-tumor activity while dampening autoimmune side effects that can be associated with immunotherapy approaches.

In some embodiments, a single-chain chimeric polypeptide can include a second antigen binding domain, wherein the second antigen binding domain can include a sequence that is at least 70% identical (e.g., at least 75% identical, at least 80% identical, at least 85% identical, at least 90% identical, at least 95% identical, at least 96% identical, at least 97% identical, at least 98% identical, at least 99% identical, or 100% identical) to SEQ ID NO: 3 or SEQ ID NO: 4.

For example, some embodiments, comprising the single-chain chimeric polypeptide binding 4-1BB set forth in WO2018-127787. The 4-1BB agonist is at present in clinical trial (NCT04903873).

Linker Sequence

In some embodiments, a single-chain chimeric polypeptide further comprises a linker sequence. In some embodiments, the linker sequence can be a flexible linker sequence. In some embodiments, the linker sequence is a synthetic linker sequence.

In some embodiments, a single-chain chimeric polypeptide further comprises a first linker sequence. In some embodiments, the first linker sequence is between the first antigen binding domain and the second antigen binding domain. In some embodiments, the first linker sequence comprises a $(G_4.5)_2$ (SEQ ID NO:6) or a 218S linker: GSTSGSGKPGSGEGSTKGS(SEQ ID NO: 9).

In some embodiments, the first linker sequence comprises a $(G_4S)_2$ linker. In some embodiments, the first linker sequence can include a sequence that is at least 70% identical (e.g., at least 75% identical, at least 80% identical, at least 85% identical, at least 90% identical, at least 95% identical, at least 96% identical, at least 97% identical, at least 98% identical, at least 99% identical, or 100% identical) to SEQ ID NO: 6.

In some embodiments, the first linker sequence comprises a 218S linker. In some embodiments, the first linker sequence can include a sequence that is at least 70% identical (e.g., at least 75% identical, at least 80% identical, at least 85% identical, at least 90% identical, at least 95% identical, at least 96% identical, at least 97% identical, at least 98% identical, at least 99% identical, or 100% identical) to SEQ ID NO: 9.

In some embodiments, a bispecific epitope binding protein includes a second antigen binding domain further comprising a second linker sequence between a second light chain and a second heavy chain. In some embodiments, the second linker sequence includes a $(G_4S)_3$ (SEQ ID NO:7) or a 218 linker (SEQ ID NO:8). In some embodiments, the second linker sequence comprises a $(G_4S)_3$ linker.

In some embodiments, the first linker sequence can include a sequence that is at least 70% identical (e.g., at least 75% identical, at least 80% identical, at least 85% identical, at least 90% identical, at least 95% identical, at least 96% identical, at least 97% identical, at least 98% identical, at least 99% identical, or 100% identical) to SEQ ID NO: 7.

It is well-understood that the designations $(G_4S)_2$, $(G_4S)_3$, and $(G_4S)_4$ refer to multimers of the pentapeptide GGGGS (or $G_4S$ or Gly4Ser). The 218 linker has the sequence: GSTSGSGKPGSGEGSTKG (SEQ ID NO: 8).

In some embodiments, a provided antigen binding domain or fragment is or comprises a humanized antibody. In some embodiments, a provided the first antigen binding domain or the second binding domain includes a human immunoglobulin constant domain, wherein the constant domain is selected from an IgG1 or a variant thereof, an IgG2 or a variant thereof, an IgG4 or a variant thereof, as well as humanized IgG1/2 or a variant thereof. In some embodiments, a provided antigen binding domain or fragment thereof is or comprises a human IgG1/2 hybrid. In some embodiments, an IgG1/2 is or comprises a sequence that is at least 95% identical to SEQ ID NO: 12.

Vectors

In some embodiments, nucleic acid constructs described above may be inserted into an expression vector or viral vector by methods known to the art, and nucleic acid molecules may be operably linked to an expression control sequence. Non-limiting examples of expression vectors include plasmid vectors, transposon vectors, cosmid vectors, and viral derived vectors (e.g., any adenoviral derived vectors (AV), cytomegaloviral derived (CMV) vectors, simian viral derived (SV40) vectors, adeno-associated virus (AAV) vectors, lentivirus vectors, and retroviral vectors). In some embodiments, the expression vector is a viral vector.

Additional sequences can be added to such cloning and/or expression sequences to optimize their function in cloning and/or expression, to aid in isolation of the polynucleotide, or to improve the introduction of the polynucleotide into a cell. Use of cloning vectors, expression vectors, adapters, and linkers is well known in the art.

In some embodiments, nucleic acid molecules are inserted into a vector that is able to express a single-chain chimeric polypeptide of the present disclosure when introduced into an appropriate cell. In some embodiments, the cell can be a eukaryotic cell. As used herein, the term "eukaryotic cell" refers to a cell having a distinct, membrane-bound nucleus. Such cells may include, for example, mammalian (e.g., rodent, non-human primate, or human), insect, fungal, or plant cells. In some embodiments, the eukaryotic cell is a yeast cell, such as *Saccharomyces cerevisiae*. In some embodiments, the eukaryotic cell is a higher eukaryote, such as mammalian, avian, plant, or insect cells. Non-limiting examples of mammalian cells include Chinese hamster ovary cells and human embryonic kidney cells (e.g., HEK293 cells).

Methods of introducing nucleic acids and expression vectors into a cell (e.g., an eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalefection, hydrodynamic delivery, magnetofection, viral transduction (e.g., adenoviral and lentiviral transduction), and nanoparticle transfection.

Methods of Producing Bispecific Epitope Binding Protein

Also provided herein are methods of producing any of the bispecific epitope binding proteins described herein that include culturing any of the cells described herein in a culture medium under conditions sufficient to result in the production of the s bispecific epitope binding protein; and recovering the bispecific epitope binding protein from the cell and/or the culture medium.

Therapeutic Applications

In some embodiments, the bispecific epitope binding protein or nucleic acid constructs described herein may be used for treating a subject in need thereof. In some embodiments, a pharmaceutical composition that includes a bispecific epitope binding protein and a pharmaceutically acceptable carrier can be administered to the subject diagnosed with a disease or condition. In some embodiments, the subject has, or is at risk for developing cancer. In some embodiments, the pharmaceutical composition can be administered with one or more additional anticancer therapies that include, but are not limited to, ionizing radiation, a chemotherapeutic agent, a therapeutic antibody, and a checkpoint inhibitor.

Cancer can refer to a broad group of diseases characterized by the uncontrolled growth of abnormal cells in the body. Unregulated cell division and growth results in the formation of malignant tumors that invade neighboring tissues and may also metastasize to distant parts of the body through the lymphatic system or bloodstream. Cancer or cancer tissue may include a tumor.

Cancers suitable for treatment by a method of the present disclosure can include, but are not limited to, bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, and prostate cancer. In some embodiments, a cancer for treatment by a method of the present disclosure can include may include, but is not limited to, carcinoma, lymphoma (e.g., Hodgkin's and non-Hodgkin's lymphomas), blastoma, sarcoma and leukemia. In some embodiments, cancer may include squamous cell carcinoma, small cell lung cancer, non-small cell lung cancer, lung adenocarcinoma, squamous cell carcinoma of the lung, peritoneal cancer, hepatocellular carcinoma, gastric cancer, pancreatic cancer, glioma, cervical cancer, ovarian cancer, liver cancer, bladder cancer, hepatocellular carcinoma, breast cancer, colon cancer, colorectal cancer, endometrial or uterine carcinoma, salivary carcinoma, kidney cancer, prostate cancer, vulvar cancer, thyroid cancer, liver carcinoma, leukemia and other lymphoproliferative disorders, and various types of head and neck cancer.

Compositions/Kits

Also provided herein are compositions (e.g., pharmaceutical compositions) that include at least one of any bispecific epitope binding proteins, any of the cells, or any of the nucleic acids described herein. In some embodiments, the compositions include at least one of any of the bispecific epitope binding proteins described herein. In some embodiments, the compositions include any of the immune cells (e.g., any of the immune cells described herein, e.g., any of the immune cells produced using any of the methods described herein).

In some embodiments, the pharmaceutical compositions are formulated for different routes of administration (e.g., intravenous, subcutaneous). In some embodiments, the pharmaceutical compositions can include a pharmaceutically acceptable carrier (e.g., phosphate buffered saline).

Single or multiple administrations of pharmaceutical compositions can be given to a subject in need thereof depending on for example: the dosage and frequency as required and tolerated by the subject. The formulation should provide a sufficient quantity of active agent to effectively treat, prevent, or ameliorate conditions, diseases, or symptoms.

Also provided herein are kits that include any of the bispecific epitope binding proteins, compositions, nucleic acids, or cells (e.g., immune cells) described herein. In some embodiments, the kits can include instructions for performing any of the methods described herein. In some embodiments, the kits can include at least one dose of any of the pharmaceutical compositions described herein.

In the context of the present description, all publications, patent applications, patents and other references mentioned herein, if not otherwise indicated, are explicitly incorporated by reference herein in their entirety for all purposes as if fully set forth, and shall be considered part of the present disclosure in their entirety.

By the present invention, the inventors have demonstrated a scaffolding for the creation of bi-, tri- or multi-specific antibodies. Specifically, an anti-4-1BB antibody domain can be produced using 94 kvt clones possessing an anti-4-1BB antibody domain (94 kvt) as a single chain Fv (scFv). The 94 kvt construct can then be used as a 4-1BB binder in other bispecific, trispecific or multispecific antibodies.

In some embodiments, the Fc region of the antibody is a IgG1/2 hybrid. By using bispecific antibody having IgG1/2 hybrid decreased ADCC and CDC effects are observed making the resulting antibody a good candidate for anti-cancer treatment in vivo and provides a better anti-tumor effect.

Unless otherwise defined, all technical and scientific terms used herein have the same meaning as commonly understood by one of ordinary skill in the art to which this disclosure belongs. In case of conflict, the present specification, including definitions, will control.

The above written description of the invention provides a manner and process of making and using it such that any person skilled in this art is enabled to make and use the same, this enablement being provided in particular for the subject matter of the appended claims, which make up a part of the original description.

As used herein, the phrases "selected from the group consisting of," "chosen from," and the like include mixtures of the specified materials.

Where a numerical limit or range is stated herein, the endpoints are included. Also, all values and subranges within a numerical limit or range are specifically included as if explicitly written out.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein.

Without being bound to the following specific embodiments, the present invention is exemplified by the follow:

(1) A bispecific epitope binding protein comprising a multimer of four single-chain chimeric polypeptides comprised of two single-chain chimeric heavy chains and two single-chain chimeric light chains wherein said bispecific epitope binding protein has a first antigen binding domain and a second antigen binding domain, wherein the first antigen binding domain binds specifically to HER2 and the second antigen binding domain binds specifically to 4-1BB.

(2) The bispecific epitope binding protein of (1), wherein
each single-chain chimeric heavy chain comprises an antibody variable region and scFv linked to CH1/Fc, and
each single-chain chimeric light chain comprises an antibody variable region linked to a C kappa region,
wherein the first antigen binding domain is formed by the antibody variable region of the single-chain chimeric heavy chain and the antibody variable region of the single-chain chimeric light chain, and
wherein the second antigen binding domain is formed by the scFv.

(3) The bispecific epitope binding protein of (2), wherein the single-chain chimeric heavy chain comprises a first linker sequence.

(4) The bispecific epitope binding protein of (3), wherein the first linker sequence is between the first antigen binding domain and the second antigen binding domain.

(5) The bispecific epitope binding protein of (3) or (4), wherein the first linker sequence comprises a $(G_4S)_2$ or a 218S linker.

(6) The bispecific epitope binding protein of (5), wherein the first linker sequence comprises a $(G_4S)_2$ linker.

(7) The bispecific epitope binding protein of any one of (1)-(6), wherein the first antigen binding domain comprises an antibody.

(8) The bispecific epitope binding protein of (7), wherein the first antigen binding domain comprises a human or humanized antibody.

(9) The bispecific epitope binding protein of any one of (1)-(8), wherein the second antigen binding domain comprises a scFv.

(10) The bispecific epitope binding protein of any one of (1)-(9), wherein the second antigen binding domain further comprises a second linker sequence between a heavy chain fragment and a light chain fragment of the scFv.

(11) The bispecific epitope binding protein of (10), wherein the second linker sequence comprises a $(G_4S)_3$ or a 218 linker.

(12) The bispecific epitope binding protein of (11), wherein the second linker sequence comprises a $(G_4S)_3$ linker.

(13) The bispecific epitope binding protein of any one of (1)-(12), wherein the antibody variable region of the single-chain chimeric heavy chain comprises a sequence that is at least 80% identical to SEQ ID NO:1.

(14) The bispecific epitope binding protein of (13), wherein the antibody variable region of the single-chain chimeric heavy chain comprises a sequence that is at least 90% identical to SEQ ID NO: 1.

(15) The bispecific epitope binding protein of (13), wherein the antibody variable region of the single-chain chimeric heavy chain comprises a sequence that is at least 95% identical to SEQ ID NO: 1.

(16) The bispecific epitope binding protein of (14), wherein the antibody variable region of the single-chain chimeric heavy chain comprises a sequence that is at least 98% identical to SEQ ID NO: 1.

(17) The bispecific epitope binding protein of (15), wherein the antibody variable region of the single-chain chimeric heavy chain comprises SEQ ID NO: 1.

(18) The bispecific epitope binding protein of any one of (1) to (13), wherein the antibody variable region of the single-chain chimeric light chain comprises a sequence that is at least 80% identical to SEQ ID NO: 2.

(19) The bispecific epitope binding protein of (18), wherein the antibody variable region of the single-chain chimeric light chain comprises a sequence that is at least 90% identical to SEQ ID NO: 2.

(20) The bispecific epitope binding protein of (19), wherein the antibody variable region of the single-chain chimeric light chain comprises a sequence that is at least 95% identical to SEQ ID NO: 2.

(21) The bispecific epitope binding protein of (20), wherein the antibody variable region of the single-chain chimeric light chain comprises a sequence that is at least 98% identical to SEQ ID NO: 2.

(22) The bispecific epitope binding protein of (21), wherein the antibody variable region of the single-chain chimeric light chain comprises SEQ ID NO: 2.

(23) The bispecific epitope binding protein of any one of (3)-(22), wherein the first linker sequence comprises a sequence that is at least 80% identical to SEQ ID NO: 6.

(24) The bispecific epitope binding protein of (23), wherein the first linker sequence comprises a sequence that is at least 90% identical to SEQ ID NO: 6.

(25) The bispecific epitope binding protein of (24), wherein the first linker sequence comprises a sequence that is at least 95% identical to SEQ ID NO: 6.

(26) The bispecific epitope binding protein of (25), wherein the first linker sequence comprises a sequence that is at least 98% identical to SEQ ID NO: 6.

(27) The bispecific epitope binding protein of (26), wherein the first linker sequence comprises SEQ ID NO: 6.

(28) The bispecific epitope binding protein of any one of (2)-(27), wherein the heavy chain fragment of the scFv comprises a sequence that is at least 80% identical to SEQ ID NO: 3 and the light chain fragment of the scFv comprises a sequence that is at least 80% identical to SEQ ID NO: 4.

(29) The bispecific epitope binding protein of (28), wherein the heavy chain fragment of the scFv comprises a sequence that is at least 90% identical to SEQ ID NO: 3 and the light chain fragment of the scFv comprises a sequence that is at least 90% identical to SEQ ID NO: 4.

(30) The bispecific epitope binding protein of (29), wherein the heavy chain fragment of the scFv comprises a sequence that is at least 95% identical to SEQ ID NO: 3 and the light chain fragment of the scFv comprises a sequence that is at least 95% identical to SEQ ID NO: 4.

(31) The bispecific epitope binding protein of (30), wherein the heavy chain fragment of the scFv comprises a sequence that is at least 98% identical to SEQ ID NO: 3 and the light chain fragment of the scFv comprises a sequence that is at least 98% identical to SEQ ID NO: 4.

(32) The bispecific epitope binding protein of (31), wherein the heavy chain fragment of the scFv comprises SEQ ID NO: 3 and the light chain fragment of the scFv comprises SEQ ID NO: 4.

(33) The bispecific epitope binding protein of any one of (10-32), wherein the second linker sequence comprises a sequence that is at least 80% identical to SEQ ID NO: 7.

(34) The bispecific epitope binding protein of (33), wherein the second linker sequence comprises a sequence that is at least 90% identical to SEQ ID NO: 7.

(35) The bispecific epitope binding protein of (34), wherein the second linker sequence comprises a sequence that is at least 95% identical to SEQ ID NO: 7.

(36) The bispecific epitope binding protein of (35), wherein the second linker sequence comprises a sequence that is at least 98% identical to SEQ ID NO: 7.

(37) The bispecific epitope binding protein of (36), wherein the second linker sequence comprises SEQ ID NO: 7.

(38) A nucleic acid molecule encoding the bispecific epitope binding protein of any one of (1)-(37).

(39) A recombinant vector comprising the nucleic acid molecule of (38).

(40) A cell comprising the nucleic acid molecule of (39).

(41) A pharmaceutical composition comprising:
any of the bispecific epitope binding proteins of any one of (1)-(37), the nucleic acid molecule of (38), the recombinant vector of (39), or the cell of (40); and a pharmaceutically acceptable carrier.

(42) A kit comprising the pharmaceutical composition of (41).

(43) A method of producing a bispecific epitope binding protein, the method comprising: culturing the cell of (40) in a culture medium under conditions sufficient to result in the production of the bispecific epitope binding protein; and recovering the bispecific epitope binding protein from the cell and/or the culture medium.

(44) A method of treating a subject in need thereof, the method comprising:
administering to the subject a composition that comprises or delivers the bispecific epitope binding protein of any one of (1)-(37), the nucleic acid molecule of (38), the recombinant vector of (39), or the cell of (40), thereby treating a disease or a condition.

(45) The method of (44), wherein the subject has, or is at risk for developing, cancer.

(46) The method of (45), wherein the cancer comprises a bladder cancer, breast cancer, cervical cancer, colon cancer, endometrial cancer, esophageal cancer, fallopian tube cancer, gall bladder cancer, gastrointestinal cancer, head and neck cancer, hematological cancer, laryngeal cancer, liver cancer, lung cancer, lymphoma, melanoma, mesothelioma, ovarian cancer, primary peritoneal cancer, salivary gland cancer, sarcoma, stomach cancer, thyroid cancer, pancreatic cancer, renal cell carcinoma, glioblastoma, prostate cancer, and combinations thereof.

Having generally described this invention, a further understanding can be obtained by reference to certain specific examples, which are provided herein for purposes of illustration only, and are not intended to be limiting unless otherwise specified.

EXAMPLES

Example 1—Bispecific Antibody 4D5×94 kvt and Variants

A bispecific antibody 4D5×94 kvt was produced, wherein anti-HER2 antibody domain was produced using 4D5 clones and anti-4-1BB antibody domain was produced using 94 kvt clones (WO2018-127787 A1). The anti-HER2 antibody domain (4D5) showed structure of an antibody while the anti-4-1BB antibody domain (94 kvt) was a single chain Fv (scFv). The two antibody domains, 4D5 and 94 kvt, were linked by a $(G_4S)_2$ or a 218S linker. The 4D5×94 kvt is bispecific epitope binding proteins assembled from a construct presented in FIG. 1B.

The bispecific antibody is multimer of four single-chain chimeric polypeptides, two heavy chains and two light chains. Each heavy chain of SEQ ID NO: 5 comprises VH, CH1, a hinge, CH2, and a CH3 and scFv and each light chain of SEQ ID NO: 13 comprises a VL domain and C kappa region.

The bispecific antibody of the invention comprises two heavy chains and two light chains, said heavy chains comprising an antibody variable region and 1 scFv linked to a Ch1/Fc region arranged N-terminus to C-terminus. The Ch1/Fc region comprises IgG1/2 hybrid, SEQ ID NO: 12 to have less ADCC and CDC effects. The bispecific antibody of the invention with almost no ADCC and CDC effects is good candidate for anti-cancer treatment in vivo

TABLE 1

4D5 × 94kvt variants and Linkers

| No. | Name | First linker | Second linker |
|---|---|---|---|
| 1 | 4D5 × 94kvt (4D5-L2 × 94kvt HLC) | $(G_4S)_2$ | $(G_4S)_3$ |
| Variants 2 | 4D5-L2 × 94kvt HLC 218 | $(G_4S)_2$ | 218 |
| 3 | 4D5-L2 × 94kvt LHC 218 | $(G_4S)_2$ | 218 |
| 4 | 4D5-218S × 94kvt HLC L3 | 218S | $(G_4S)_3$ |
| 5 | 4D5-218S × 94kvt HLC 218 | 218S | 218 |
| 6 | 4D5-218S × 94kvt LHC218 | 218S | 218 |

Figure 2:
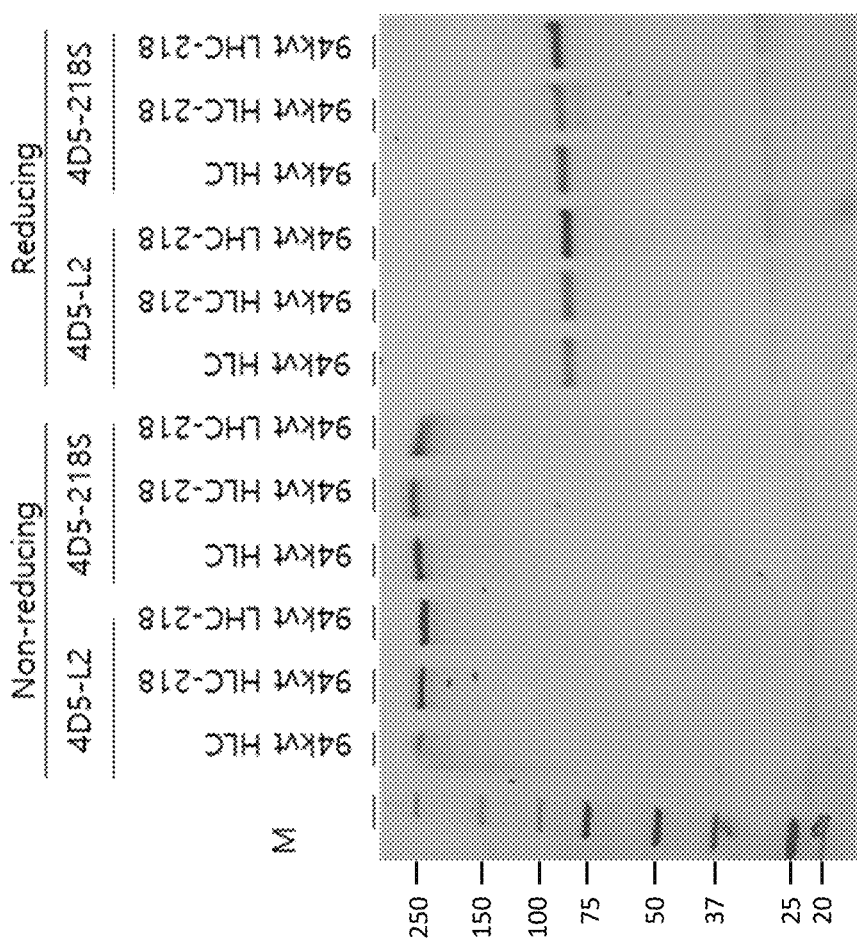
FIG. 2 shows SDS-PAGE results with the anti-HER2/anti-4-1BB bispecific antibodies (4D5×94 kvt and variants) in a non-reducing and reducing condition.
Figure 3:
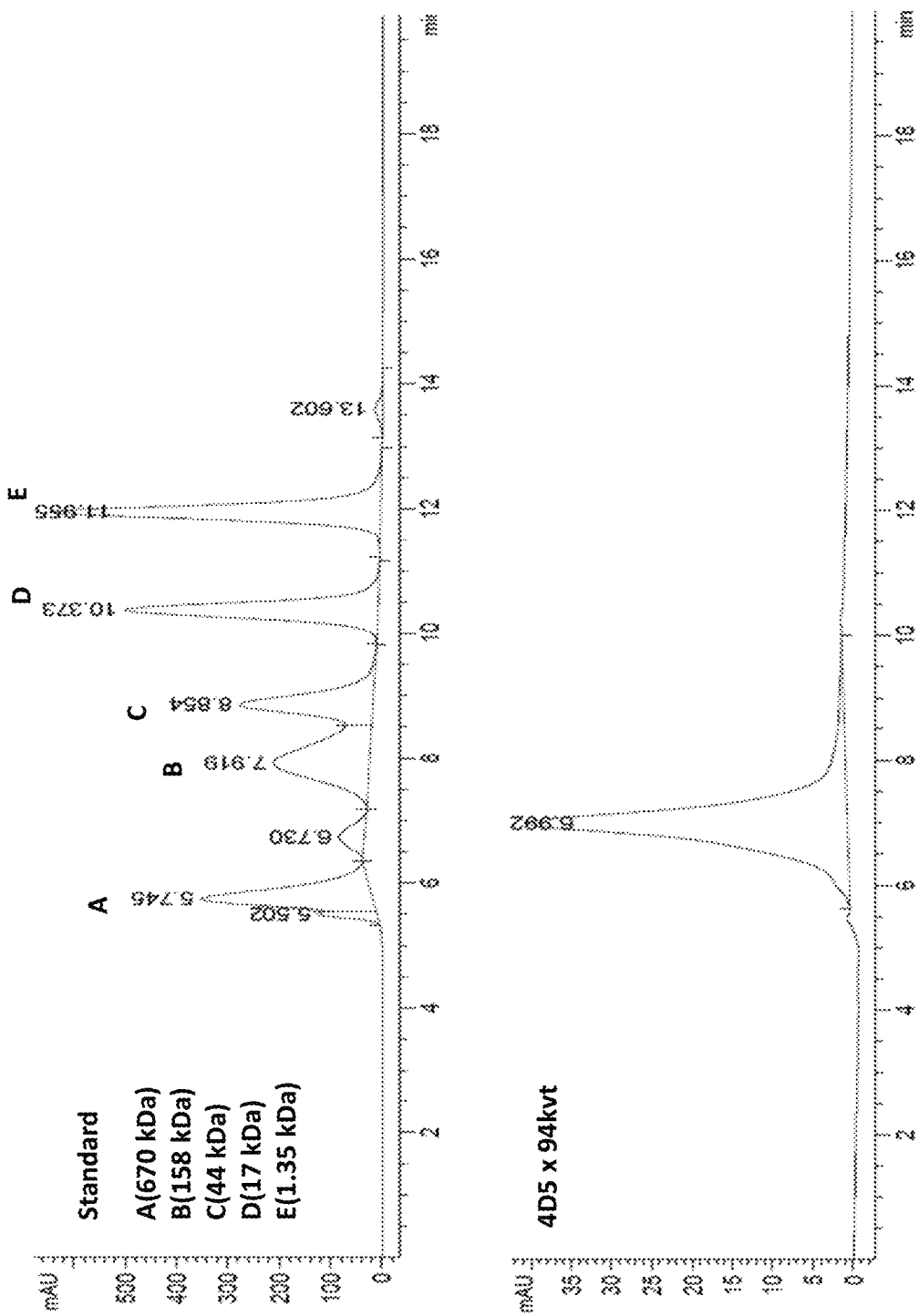
FIG. 3 shows a size exclusion chromatography graph with 4D5×94 kvt.

The heavy chain was cloned using an expression vector pcDNA3.3 or pd18 and the light chain was cloned using pOptiVEC. The bispecific antibody 4D5×94 kvt and variants were produced using transient transfection in Expi293F cells and then purified with a protein A column. SDS-PAGE results show 4D5×94 kvt and variants at about 200 kDa in non-reducing conditions and the heavy chain at 75 kDa, light chain at 25 kDa in reducing conditions (FIG. 2). SEC analysis results of 4D5×94 kvt show a single peak between 670 kDa and 158 kDa (FIG. 3).

Example 2—Cell Binding Assay

Cell lines with high expression of HER2, such as SKOV3 (human ovarian cancer cell, JCRB, JCRB1549) and SKBR3 (human breast cancer cell, JCRB, JCRB1627.1), cell lines with low expression of HER2, such as MCF-7 (human breast cancer cell), MDA-MB-231 (human breast cancer cell, JCRB, JCRB1559), 4-1BB jurkat (in house generated), 293T-4-1BB NFkB-Luc (in house generated) and human T cells activated by anti-CD3 antibodies were used as a 4-1BB positive cell line.

Figure 4A:
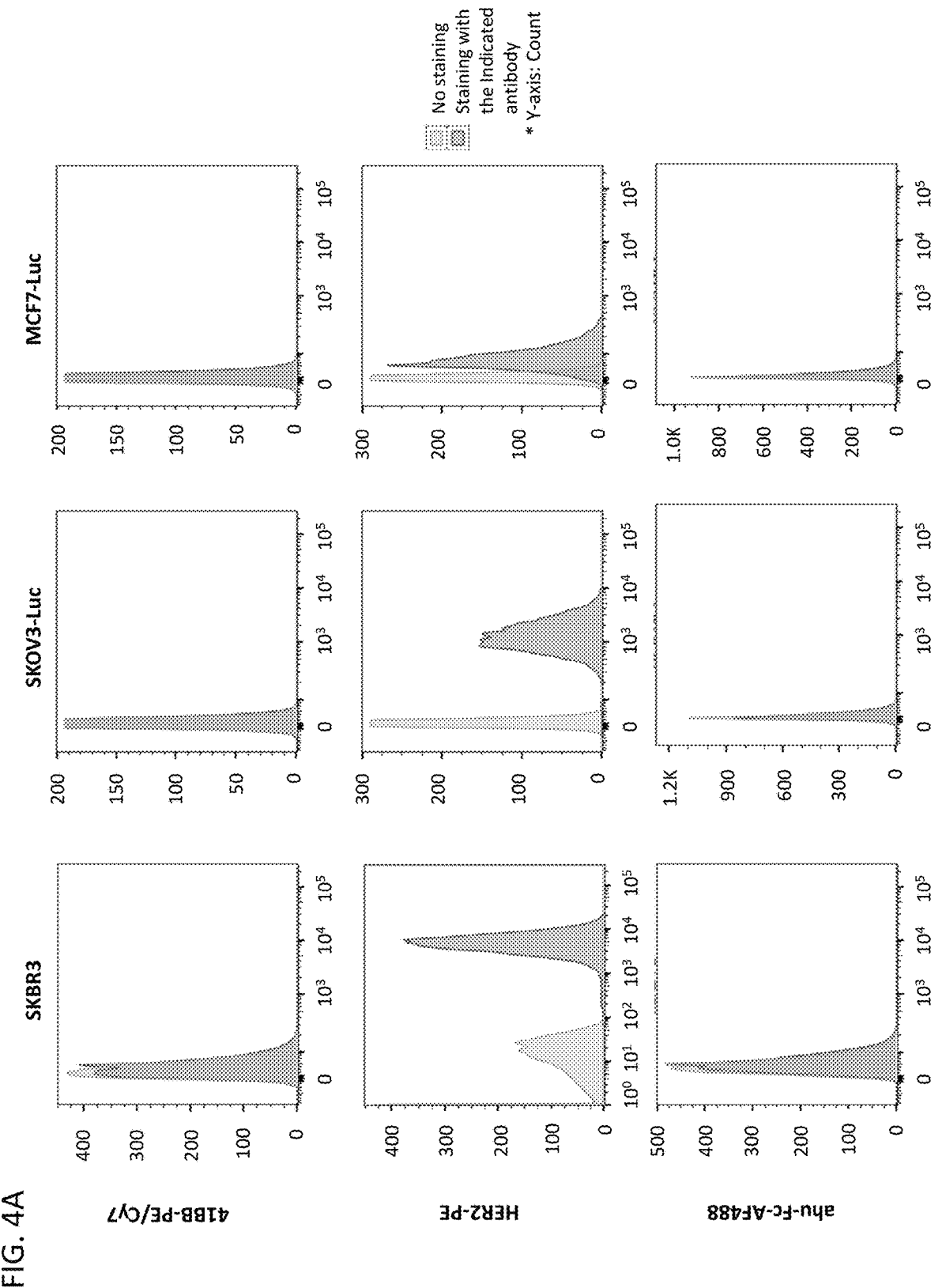
Figure 5A:
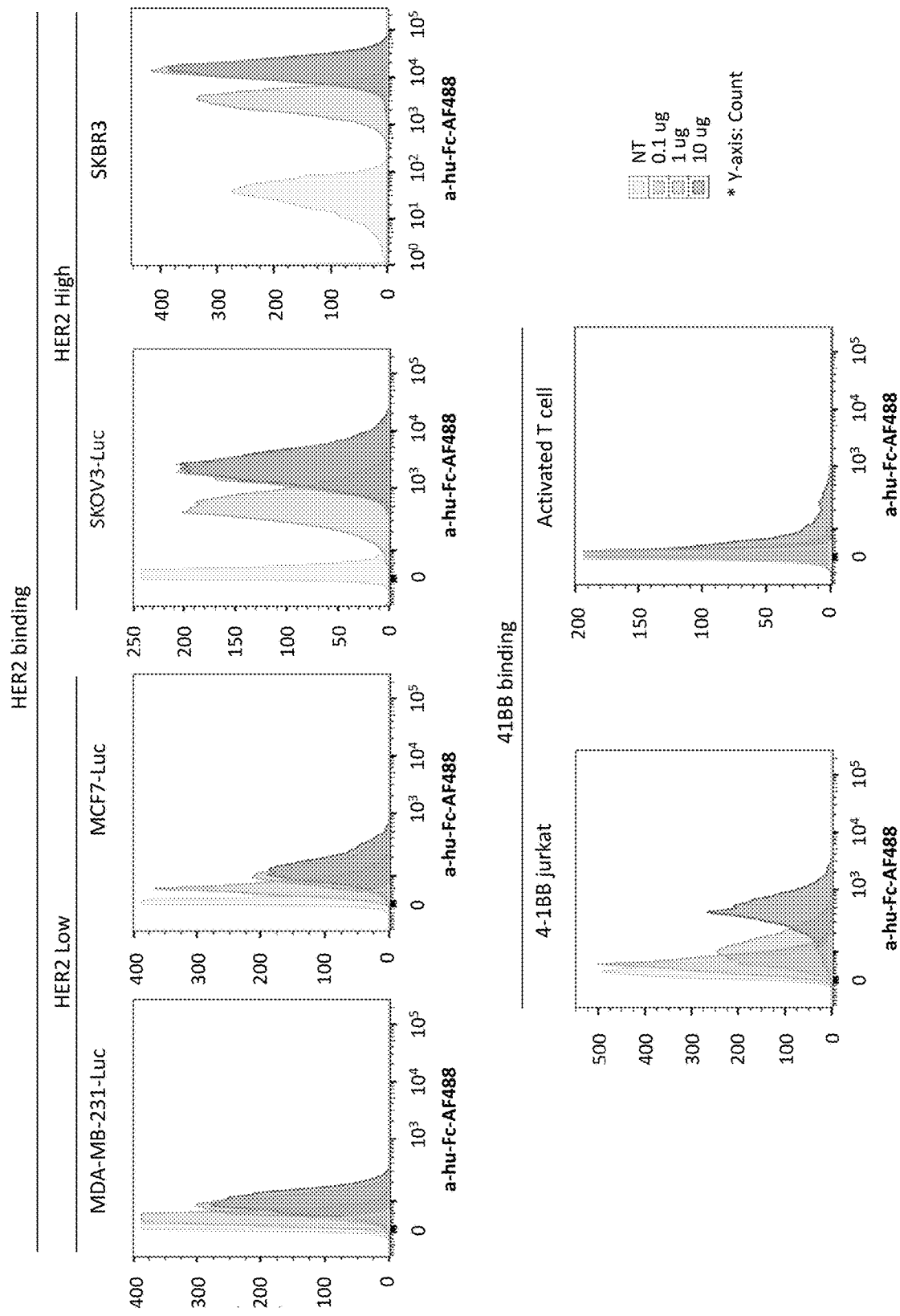
FIG. 5A, FIG. 5B, and FIG. 5C show cell binding assay results of 4D5×94 kvt with cells expressing HER2 and 4-1BB.
Figure 5B:
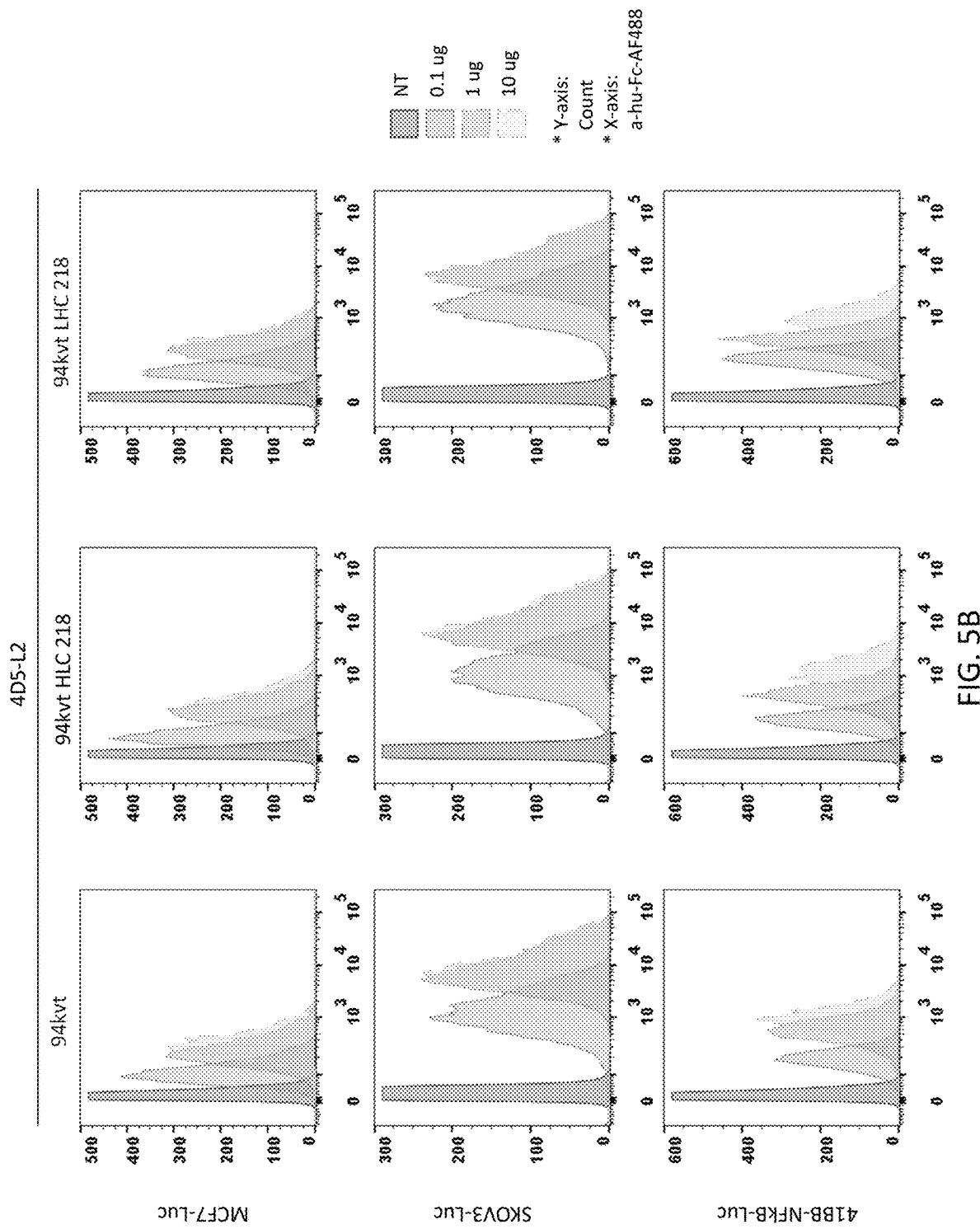
Figure 5C:
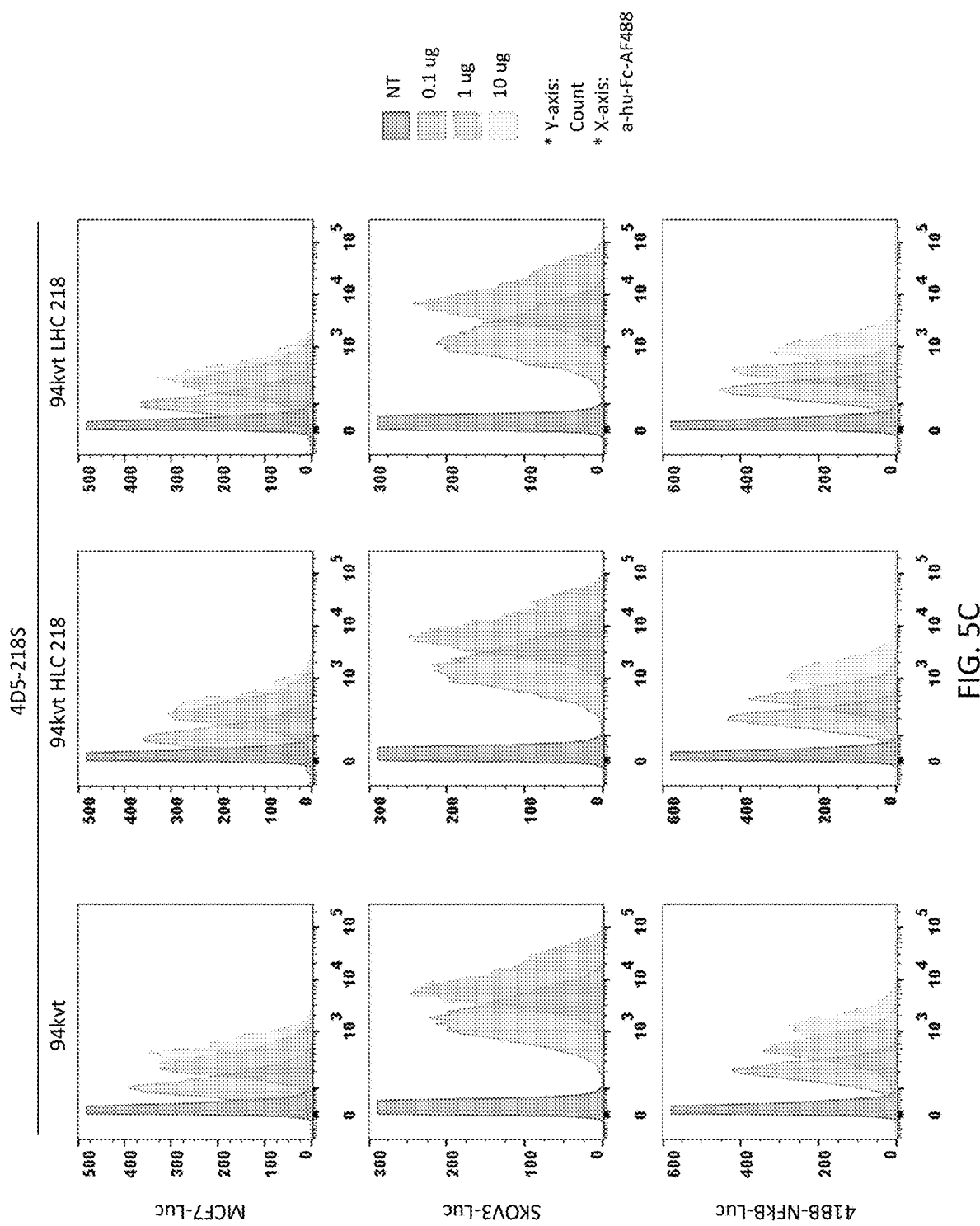

T cells were obtained from peripheral blood mononuclear cells (PBMCs) from blood collected using ficoll separation and Pan T negative selection. Separated T cells were plated on a 12 well plate O/N coated with anti-CD3 antibody at a concentration of 1 μl and activated for 48 hours. $2 \times 10^5$ cells were incubated with 4D5×94 kvt at final concentration of 10, 1, 0.1 μg/ml for 20 minutes at 4° C. The cells were washed FACS washing buffer and then treated with anti-hFC-488 second antibodies at 1 μl/tube for 20 minutes. The cells were then washed twice before FACS analysis. FIG. 4A-FIG. 4C show HER2 and 4-1BB expression to levels in each cell line. SKOV3 and SKBR3 cell lines show high HER2 expression, MCF-7 and MDA-MB-231 cell lines show low HER2 expression, while 4-1BB Jurkat and activated T cells did not show HER2 expression. 4-1BB expression was only observed in 4-1BB Jurkat and activated T cells. FACS analysis results show 4D5×94 kvt (FIG. 5A) and variants (FIG. 5B-FIG. 5C) binding to HER2 and 4-1BB positive cell lines in a dose dependent manner.

Example 3—Dual Antigen Binding Assay

Figures 6A, 6B:
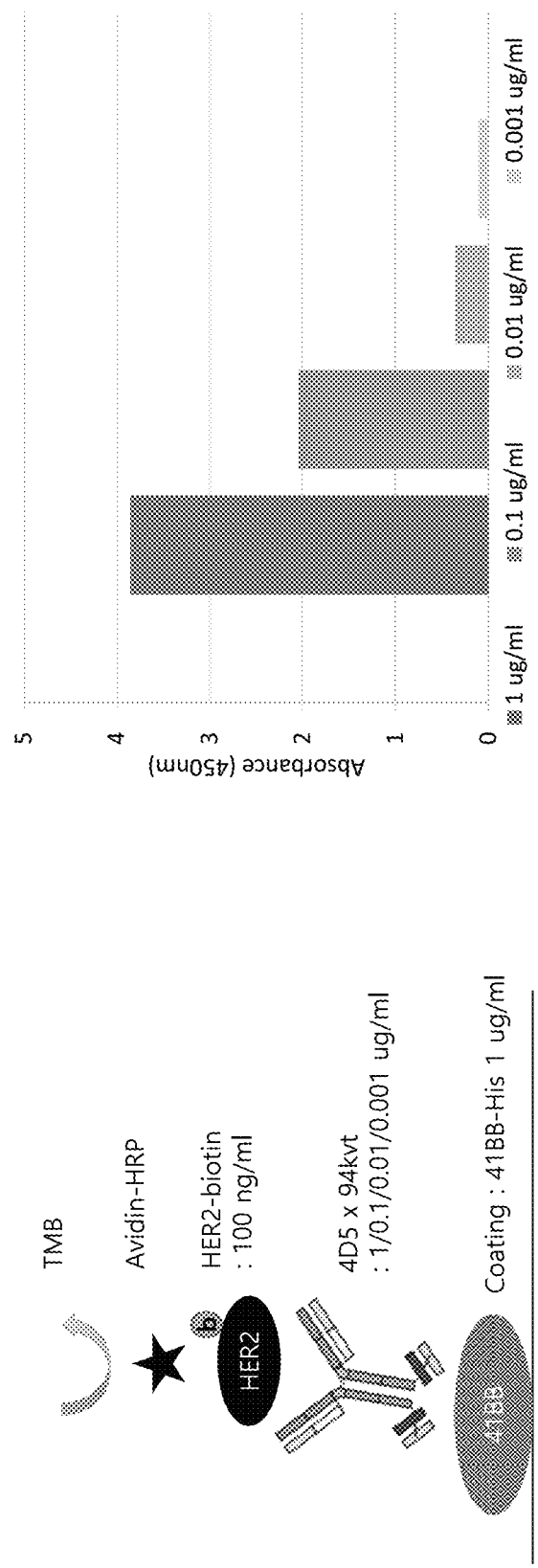
FIG. 6A shows an exemplary schematic of a dual antigen binding assay with 4D5×94 kvt.
FIG. 6B is a graph of dual antigen binding assay results showing dose dependent binding of 4D5×94 kvt to both HER2 and 4-1BB.

Dual binding assay was performed to analyze 4D5×94 kvt binding to both antigens HER2 and 4-1BB. Assay protocol is shown in FIG. 6A. Briefly, 41BB antigen at a concentration of 1 ug/ml was coated on a 96 well immunoplate with O/N at 4° C., and then 300 μl of 1× assay buffer (Biolegend) was treated for 1 hour to block non-specific binding. After 1, 0.1, 0.01, 0.001 μg/ml of 4D5×94 kvt was treated for 2 hours, 100 ng/ml of 100 μl of HER2-Biotin antigen was treated and incubated for 2 hours. Avidin-HRP was diluted 1/1000 and treated with 100 μl for 20 minutes, followed by color development with TMB, and then the reaction was stopped using sulfuric acid. Washing was performed 4 times using washing buffer in all proHER2es except for the proHER2 after TMB treatment, and all proHER2es except for the 4-1BB coating proHER2 were carried out at room temperature.

The results confirm that 4D5×94 kvt simultaneously binds to both antigens 41BB and HER2 in a dose-dependent manner and that anti-HER2 antibodies and anti-4-1BB antibodies do not affect specific antigen binding while maintaining binding affinity (FIG. 6B).

Example 4—Analyzing Affinity to HER2 and 4-1BB

The affinity of 4D5×94 kvt to HER2 and 4-1BB, was analyzed using surface plasmon resonance (SPR). 4D5× Utomilumab (PF-05082566, 4D5×Uto) was used as control. Results to are shown in Table 2.

TABLE 2

Summary of binding kinetics

| Analyte | BsAB | | Ka ($\times 10^5$, 1/Ms) | Kd ($\times 10^{-4}$, 1/s) | KD ($\times 10^{-9}$, M) |
|---|---|---|---|---|---|
| HER2-His | 4D5-L2 | 94kvt | 1.1 | 3 | 2.8 |
| | | Utomilumab | 1.1 | 3.2 | 2.9 |
| 41BB-His | 4D5-L2 | 94kvt | 9.1 | 4 | 4 |
| | | Utomilumab | 17.2 | 29.2 | 17 |

Example 5—Dual Cell Binding Assay

Figure 7A:
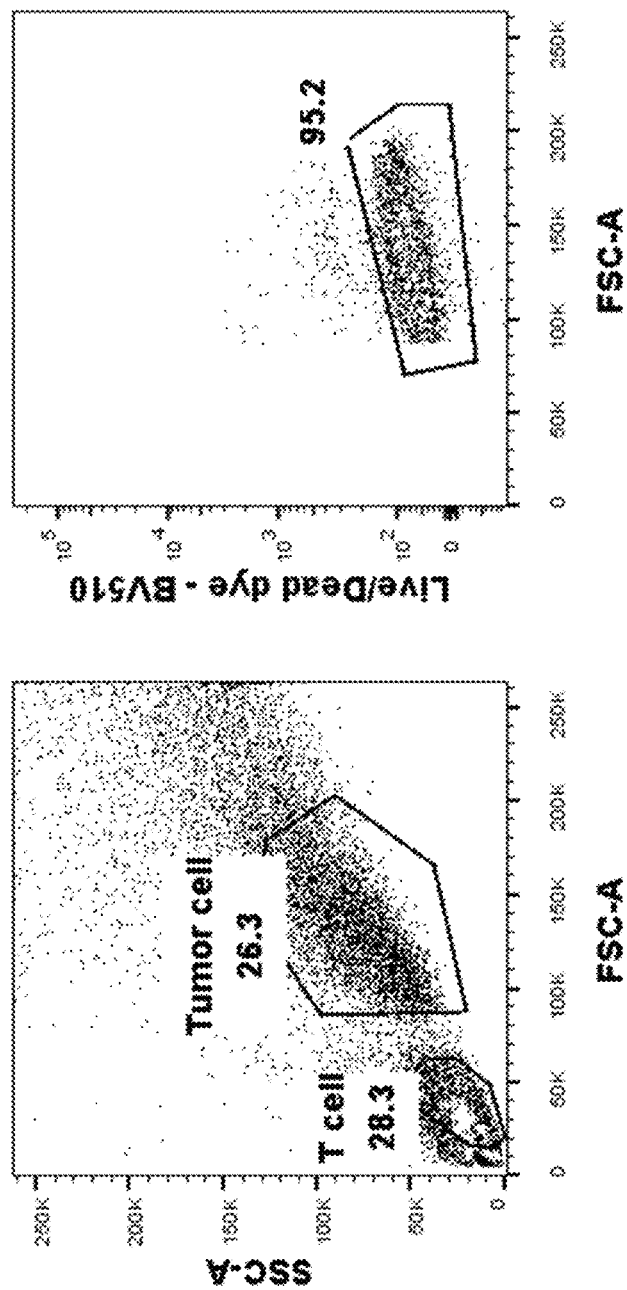
FIG. 7A shows gating information of the dual cell binding assay.
Figure 7B:
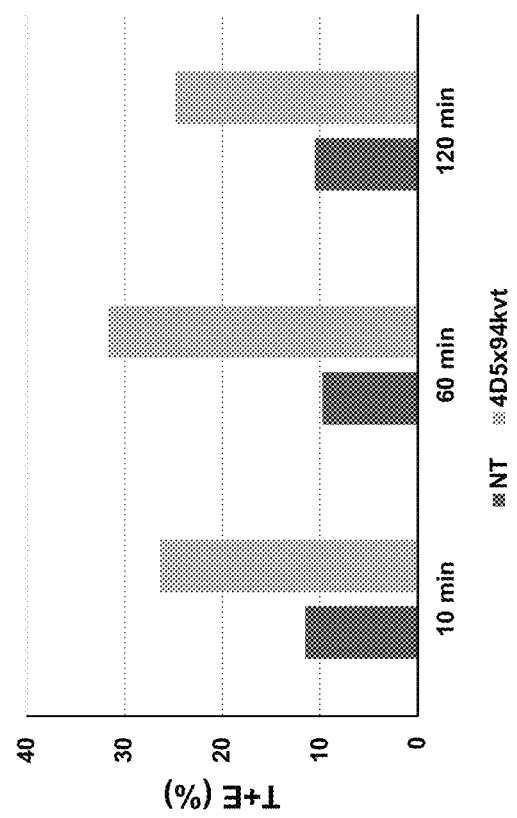
FIG. 7B shows results from a dual cell binding assay with 4D5×94 kvt

Dual cell binding assay was performed to analyze the increase of binding between tumor cells and T cells when treated with 4D5×94 kvt. EBV specific T cells were seeded on a 12 well plate coated with 100 ng/ml anti-CD3 antibody for O/N and incubated at 4° C. for 24 hours. Tumor cells were stained with CFSE cell trace. $2 \times 10^5$ cells T cells and $2 \times 10^5$ tumor cells (T cell: Tumor cell=1:1) were incubated together in two groups wherein one group was treated with 4D5×94 kvt. The cells were incubated for 10, 60 and 120 minutes. After incubation, the cells were live/dead stained at 4° C. for 10 minutes, then stained with BV450 conjugated anti-CD8 antibodies at 4° C. for 15 minutes before performing FACS analysis. Results show 2-3 times increased binding between tumor cells and T cells treated with 4D5×94 kvt (FIG. 7A-7B). As a result of the dual cell binding assay, it was observed that tumor cells and T cells were bound without 4D5×94 kvt treatment, but cell-cell binding increased by 2-3 times or more when 4D5×94 kvt was treated.

Example 6—IFN-γ Secretion Assay

IFN-γ secretion assay was performed to analyze T cell activation by 4D5×94 kvt with different antigen concentrations. For Anti-CD3 anti-body 100 ng/ml, coating was carried out at 4° C. on 96 well plates with O/N for both conditions with and without HER2 antigen 1 ug/ml. BsAB was incubated with 10, 1, and 0.1 ng/ml at 100 µl at 37° C. for 1 hour, then treated with 1×10⁴ cells/100 µl/well of EBV specific T cells, and incubated at 37° C. in a $CO_2$ incubator for 68 hours. After incubation, the cells were downed by centrifugation, the supernatant was harvested, and IFN-γ ELISA was performed thereon. ELISA was performed according to the Biolegend protocol.

Figure 8:
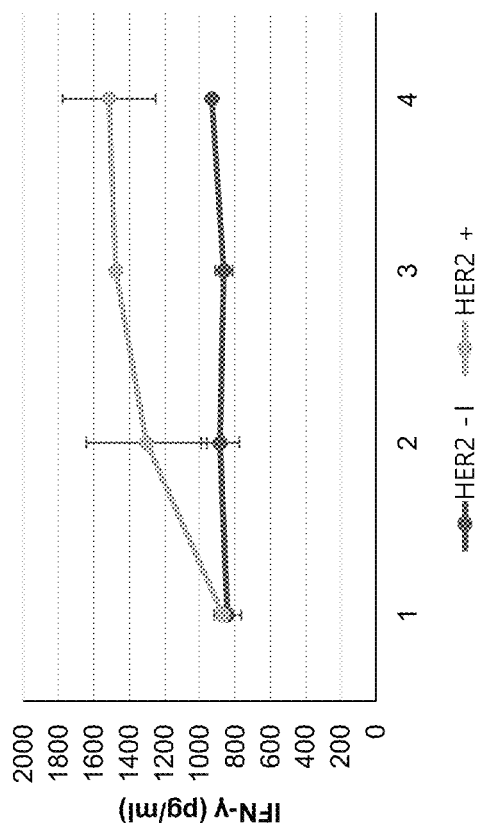
FIG. 8 is a graph of IFN-γ secretion assay results showing increased secretion of IFN-γ with 4D5×94 kvt binding to HER2.

ELISA results show increased IFN-γ secretion in the group treated with 4D5×94 kvt (FIG. 8). Specifically, it can be seen that 4D5×94 kvt is antigen-dependent and specifically helps in the activation of T cells. IFN-γ secretion did not increase in the group not coated with HER2 even when the concentration of 4D5×94 kvt increased, whereas in the group coated with HER2, the secretion of IFN-γ increased as the concentration of 4D5×94 kvt increased.

Example 7—Killing Assay

Figure 9:
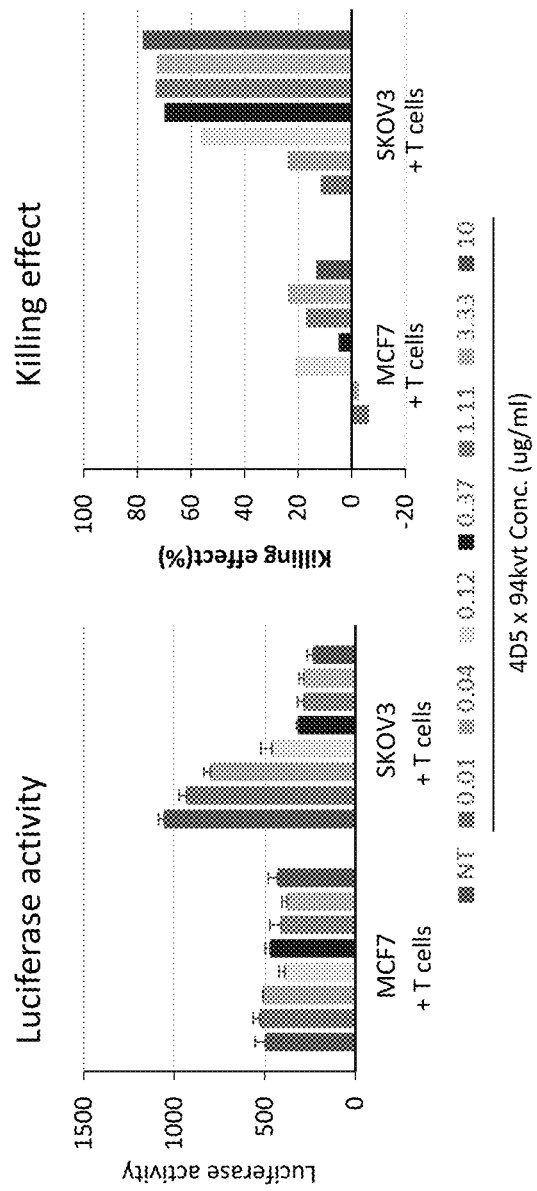
FIG. 9 shows results from a cell killing assay with 4D5×94 kvt.
Figure 10:
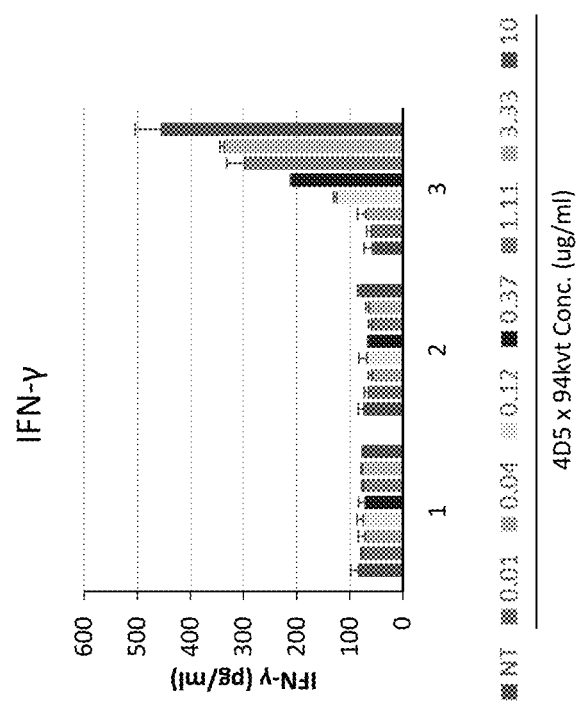
FIG. 10 shows measurements of IFN-γ in cells using ELISA.

Killing assay was performed to analyze tumor cell killing by T cells activated with 4D5×94 kvt. Cell lines, SKOV3 with high HER2 expression and MCF7 with low HER2 expression were used as tumor cell lines with stable luciferase activity. Tumor cells were prepared as described in Example 2 and activated with anti-CD3 antibodies at 1 µg/ml concentration on an O/N coated plate at 4° C. for 72 hours. Tumor cells were then seeded in a 96 well white plate at 1×10⁴ cells/100 µl/well one day before treating with 4D5×94 kvt. 4D5×94 kvt was used at concentrations starting from 10 µg/ml and final concentration was made 10 µl/well before treatment. T cells were obtained from the anti-CD3 antibody coated plate and 4-1BB marker was used to determine activation of the T cells. Activated T cells were treated at a ratio of Tumor cell: T cells=1:0.125, then treated with 4D5×94 kvt and incubated at 37° C. for 72 hours in a $CO_2$ incubator. After incubation and centrifugation, the supernatant was collected for IFN-γ ELISA and the cells were treated with luciferin for luciferase assay. Results are shown in FIGS. 9 and 10. As a result of Luciferase assay, no significant difference was observed with or without 4D5×94 kvt treatment in the HER2 low expressed cell line, MCF7. On the other hand, when 4D5×94 kvt was treated in SKOV3, a HER2 high expressed cell line, a dose-dependent killing effect was observed. Similarly to the killing assay, IFN-γ production was not observed in the group treated with 4D5×94 kvt in MCF7, whereas in the group treated with 4D5×94 kvt in SKOV3, it was confirmed that IFN-γ production increased in a dose-dependent manner.

Example 8—In Vivo Efficacy Assay 1

Figure 11:
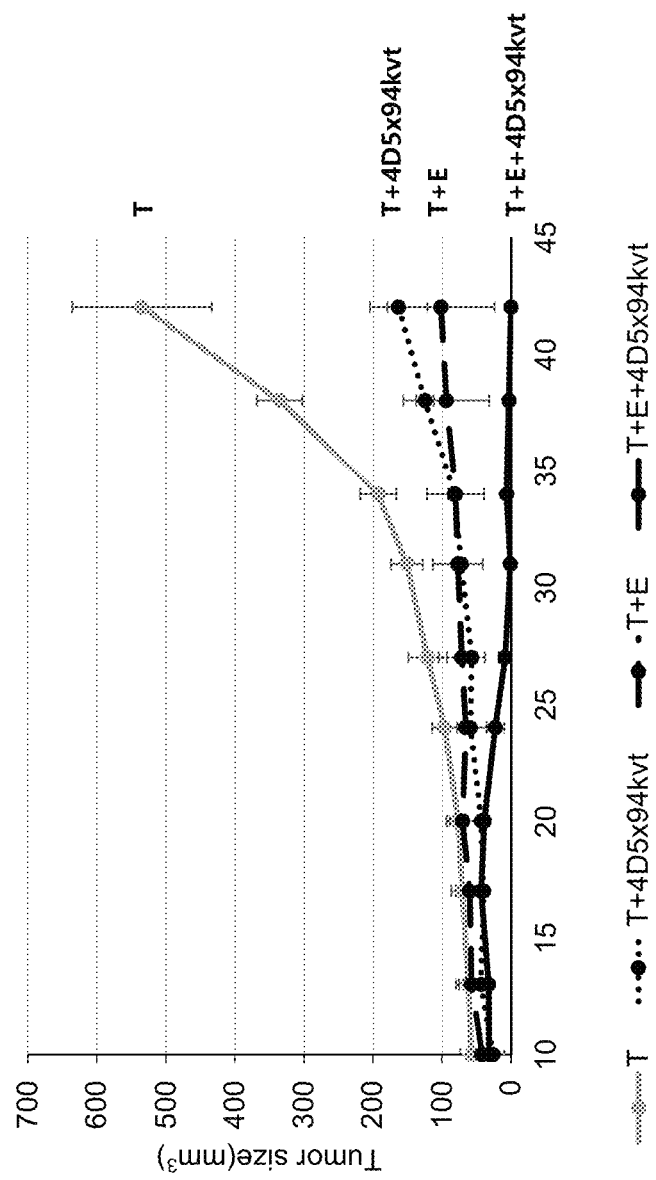
FIG. 11 is a graph showing results of an in vivo tumor growth inhibition study 1.

In vivo efficacy assay was performed to analyze effectiveness of 4D5×94 kvt by measuring tumor growth inhibition. The experiment was performed using an immunodeficient mouse, NSG female. SKOV3 cell line was used for tumor cells and T cells were activated with anti-CD3 antibody for 72 hours. 1×10⁷ tumor cells and 4.7×10⁵ activated T cells were used at a Tumor cell (T): Effector T cell (E)=1:0.05 ratio. 200 µg of 4D5×94 kvt was mixed with the cells and injected. Anti-HER2 antibody domain (4D5) and anti-4-1BB antibody domain (94 kvt) were used as a control. In the case of 4D5 single antibody and 94 kvt single antibody used as controls, 153 µg, 1.3 times less, was administered in consideration of the molecular weight of the double antibody. The dose was administered at 200 µl. Tumor size was measured twice a week after one week post injection. Results are shown in FIG. 11. As a result of observation of tumor size, it was confirmed that when tumor cells were treated with activated T cells and 4D5×94 kvt, tumor growth was clearly inhibited compared to the group treated with only T cells and the group treated with only 4D5×94 kvt.

Example 9—In Vivo Efficacy Assay 2

In h4-1BB knock-in mice that Human 4-1BB is expressed, hHER2-MC38 cells, which are mouse cancers in which human HER2 is expressed, were s.c injected on the back; control antibody (anti-HER2 antibody) and 4D5×94 kvt were administered at the time the tumor grew by about 200-300 mm³. The administration of antibody was i.v injected, the concentration was 4D5×94 kvt 2.5 mg/kg, and 100 µl was injected, and the antibody was administered 1.3 times less in consideration of the molecular weight. Administration was administered 5 times at 3-day intervals, and tumor size was observed until 4 days after the last administration. In addition, to confirm toxicity, blood was collected on the day of the end of the experiment and the concentrations of ALT (alanine aminotransferase), AST (aspartate aminotransferase) and BUN (Blood Urea Nitrogen) in the blood were checked using a biochemical analyzer.

Figure 12:
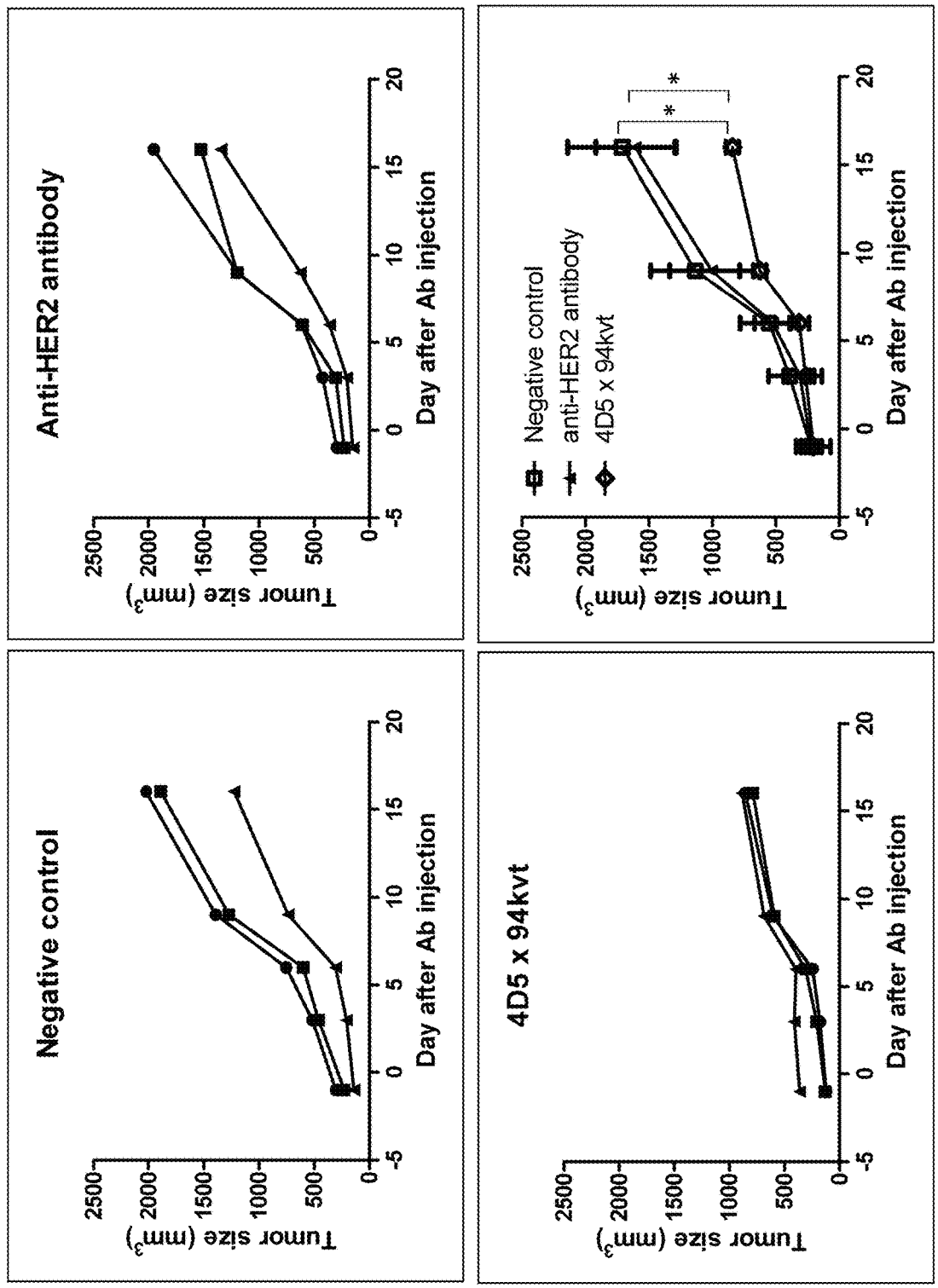
FIG. 12 is a graph showing results of an in vivo tumor growth inhibition study 2.

As a result of the tumor size reduction experiment, in the case of anti-HER2 antibody group, the tumor grew without difference from negative control group, but in the case of 4D5×94 kvt group, the tumor decreased by about 50%. (FIG. 12)

As a result of the indicator analysis for hepatotoxicity in the 4D5×94 kvt-administered group, the normal range of ALT is 17-77 U/L, which appeared as 19.0±1.2, AST, the normal range is 54-298 U/L, which appeared as 63.0±5.3, and BUN, the normal range is 8-33 mg/dL which appeared as 17.7±0.9; all were confirmed to be within the normal range, and it can be concluded that there is no hepatotoxicity within the experimental conditions. (Table 3)

TABLE 3

| Results of analysis of liver function markers | | | |
|---|---|---|---|
| | ALT (U/L) | AST (U/L) | BUN (mg/dL) |
| Normal | 17-77 | 54-298 | 8-33 |
| Negative control | 21.7 ± 2.3 | 77.0 ± 11.1 | 18.0 ± 0.8 |
| anti-HER2 antibody | 19.7 ± 1.2 | 71.7 ± 4.2 | 21.0 ± 1.3 |
| 4D5 × 94kvt | 19.0 ± 1.2 | 63.0 ± 5.3 | 17.7 ± 0.9 |

Example 10—Exemplary Sequences of 4D5 ccx94 kvt bi-Specific Antibodies

Figure 13A:
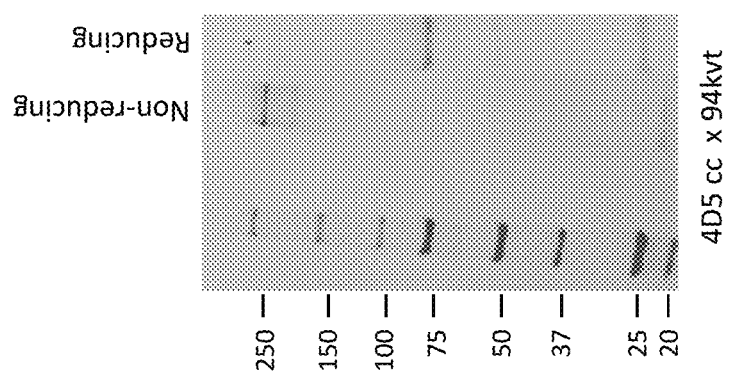
FIG. 13A shows SDS-PAGE results with the 4D5 cc×94 kvt in a non-reducing and reducing condition.

An additional exemplary sequence of an anti-HER2/anti-4-1BB bispecific antibody includes the variant 4D5 ccx94 kvt, wherein the amino acid sequence of 4D5 VH G44C comprises a sequence of SEQ ID NO: 10 and the amino acid sequence of 4D5 VL Q100C comprises a sequence of SEQ ID NO: 11. SDS-PAGE result shows another anti-HER2/anti-4-1BB bispecific antibody, 4D5 ccx94 kvt (FIG. 13A).

Figure 13B:
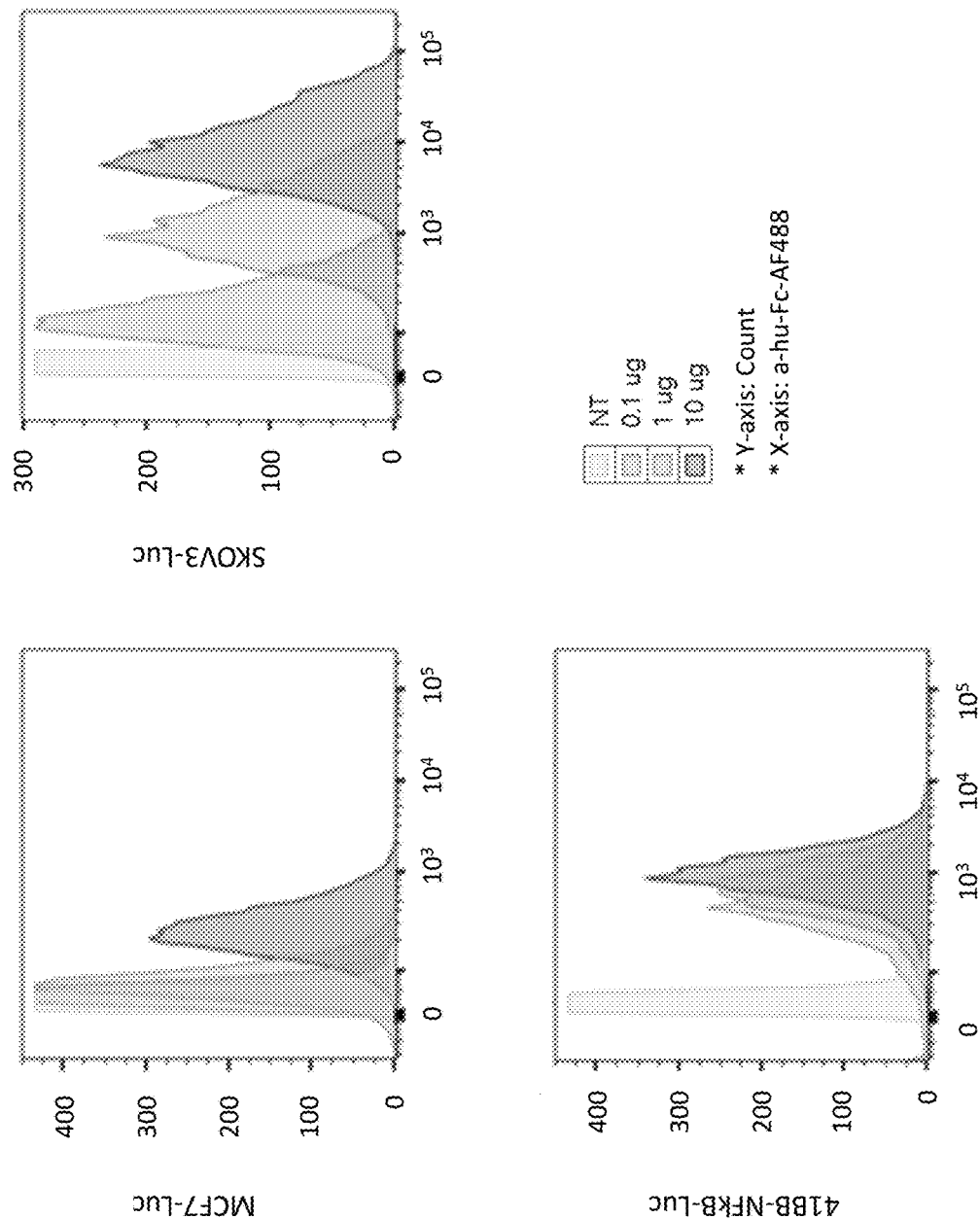
FIG. 13B shows cell binding assay results of 4D5 cc×94 kvt with cells expressing HER2 and 4-1BB.

A graph of dual antigen binding assay results shows dose dependent binding of 4D5 ccx94 kvt to both HER2 and 4-1BB (FIG. 13B).

Numerous modifications and variations on the present invention are possible in light of the above teachings. It is, therefore, to be understood that within the scope of the accompanying claims, the invention may be practiced otherwise than as specifically described herein.

What we claim is:

1. A bispecific epitope binding protein comprising a multimer of four single-chain chimeric polypeptides comprised of two single-chain chimeric heavy chains and two single-chain chimeric light chains wherein said bispecific epitope binding protein has a first antigen binding domain and a second antigen binding domain, wherein the first antigen binding domain binds specifically to HER2 and the second antigen binding domain binds specifically to 4-1BB, wherein:

the first antigen binding domain comprises an antibody, wherein the antibody variable region of the single-chain chimeric heavy chain comprises a sequence having 100% identity to the three CDRs of SEQ ID NO: 1 and the antibody variable region of the single-chain chimeric light chain comprises a sequence having 100% identity to the three CDRs of SEQ ID NO: 2, and the second antigen binding domain comprises a scFv, wherein the heavy chain variable domain of the scFv comprises a sequence having 100% identity to the three CDRs of SEQ ID NO: 3 and the light chain variable domain of the scFv comprises a sequence having 100% identity to the three CDRs of SEQ ID NO: 4.

2. The bispecific epitope binding protein of claim 1, wherein the antibody variable region of the single-chain chimeric heavy chain comprises a sequence having 100% identity to the three CDRs of SEQ ID NO: 1 and that has an overall degree of homology that is at least 95% identical to SEQ ID NO: 1.

3. The bispecific epitope binding protein of claim 1, wherein the antibody variable region of the single-chain chimeric light chain comprises a sequence having 100% identity to the three CDRs of SEQ ID NO: 2 and that has an overall degree of homology that is at least 95% identical to SEQ ID NO: 2.

4. The bispecific epitope binding protein of claim 1, wherein the heavy chain variable domain of the scFv comprises a sequence having 100% identity to the three CDRs of SEQ ID NO: 3 and that has an overall degree of homology that is at least 95% identical to SEQ ID NO: 3.

5. The bispecific epitope binding protein of claim 1, wherein the light chain variable of the scFv comprises a sequence having 100% identity to the three CDRs of SEQ ID NO: 4 and that has an overall degree of homology that is at least 95% identical to SEQ ID NO: 4.

6. The bispecific epitope binding protein of claim 1, wherein the first antigen binding domain comprises a humanized antibody.

7. The bispecific epitope binding protein of claim 1, wherein
each single-chain chimeric heavy chain comprises an antibody variable region, CH1/Fc region and the scFv, wherein the scFv is linked to the CH1/Fc region, and
each single-chain chimeric light chain comprises an antibody variable region linked to a C kappa region,
wherein the first antigen binding domain is formed by the antibody variable region of the single-chain chimeric heavy chain and the antibody variable region of the single-chain chimeric light chain, and
wherein the second antigen binding domain is formed by the scFv.

8. The bispecific epitope binding protein of claim 7, wherein the antibody variable region of the single-chain chimeric heavy chain comprises a sequence having 100% identity to the three CDRs of SEQ ID NO: 1 and that has an overall degree of homology that is at least 95% identical to SEQ ID NO: 1.

9. The bispecific epitope binding protein of claim 8, wherein the antibody variable region of the single-chain chimeric heavy chain comprises SEQ ID NO: 1.

10. The bispecific epitope binding protein of claim 7, wherein the antibody variable region of the single-chain chimeric light chain comprises a sequence having 100% identity to the three CDRs of SEQ ID NO: 2 and that has an overall degree of homology that is at least 95% identical to SEQ ID NO: 2.

11. The bispecific epitope binding protein of claim 10, wherein the antibody variable region of the single-chain chimeric light chain comprises SEQ ID NO: 2.

12. The bispecific epitope binding protein of claim 7, wherein the heavy chain variable domain of the scFv comprises a sequence having 100% identity to the three CDRs of SEQ ID NO: 3 and that has an overall degree of homology that is at least 95% identical to SEQ ID NO: 3.

13. The bispecific epitope binding protein of claim 12, wherein the heavy chain variable domain of the scFv comprises SEQ ID NO: 3.

14. The bispecific epitope binding protein of claim 7, wherein the light chain variable of the scFv comprises a sequence having 100% identity to the three CDRs of SEQ ID NO: 4 and that has an overall degree of homology that is at least 95% identical to SEQ ID NO: 4.

15. The bispecific epitope binding protein of claim 6, wherein the light chain variable domain of the scFv comprises SEQ ID NO: 4.

16. The bispecific epitope binding protein of claim 7, wherein the single-chain chimeric heavy chain comprises a first linker sequence.

17. The bispecific epitope binding protein of claim 16, wherein the first linker sequence is between the first antigen binding domain and the second antigen binding domain.

18. The bispecific epitope binding protein of claim 16, wherein the first linker sequence comprises a $(G_4S)_2$ or a 218S linker.

19. The bispecific epitope binding protein of claim 16, wherein the first linker sequence comprises a sequence that is at least 97% identical to SEQ ID NO: 6.

20. The bispecific epitope binding protein of claim 16, wherein the first linker sequence comprises a $(G_4S)_2$ linker having the sequence of SEQ ID NO: 6.

21. The bispecific epitope binding protein of claim 7, wherein the second antigen binding domain further comprises a second linker sequence between the heavy chain variable domain ($V_H$) and light chain variable domain ($V_L$) of the scFv.

22. The bispecific epitope binding protein of claim 21, wherein the second linker sequence comprises a $(G_4S)_3$ or a 218 linker.

23. The bispecific epitope binding protein of claim 22, wherein the second linker sequence comprises a $(G_4S)3$ linker having the sequence of SEQ ID NO: 7.

24. A pharmaceutical composition comprising:
a bispecific epitope binding protein of claim 1, a nucleic acid molecule encoding said bispecific epitope binding protein, a recombinant vector comprising said nucleic acid molecule encoding said bispecific epitope binding protein, or a cell comprising said nucleic acid molecule encoding said bispecific epitope binding protein; and
a pharmaceutically acceptable carrier.

25. A kit comprising the pharmaceutical composition of claim 24.

* * * * *